(12) United States Patent
Cao et al.

(10) Patent No.: US 11,866,494 B2
(45) Date of Patent: Jan. 9, 2024

(54) CAR T THERAPY THROUGH USES OF CO-STIMULATION

(71) Applicant: Innovative Cellular Therapeutics Co., Ltd., Grand Cayman (KY)

(72) Inventors: Zhiyuan Cao, Shanghai (CN); Chengfei Pu, Shanghai (CN); Lei Xiao, Shanghai (CN); Zhao Wu, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 643 days.

(21) Appl. No.: 16/552,521

(22) Filed: Aug. 27, 2019

(65) Prior Publication Data

US 2020/0071400 A1    Mar. 5, 2020

Related U.S. Application Data

(60) Provisional application No. 62/725,967, filed on Aug. 31, 2018.

(51) Int. Cl.
| | | |
|---|---|---|
| *C07K 14/725* | (2006.01) | |
| *C12N 5/0783* | (2010.01) | |
| *C07K 16/30* | (2006.01) | |
| *A61K 39/395* | (2006.01) | |
| *A61K 35/17* | (2015.01) | |
| *A61P 35/00* | (2006.01) | |
| *C07K 16/28* | (2006.01) | |
| *C07K 14/705* | (2006.01) | |
| *A61K 38/00* | (2006.01) | |

(52) U.S. Cl.
CPC .......... *C07K 16/2803* (2013.01); *A61K 35/17* (2013.01); *C07K 14/7051* (2013.01); *C07K 14/70521* (2013.01); *C07K 14/70532* (2013.01); *C07K 14/70578* (2013.01); *C12N 5/0636* (2013.01); *A61K 38/00* (2013.01); *C07K 2317/24* (2013.01); *C07K 2317/55* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 9,402,865 B2* | 8/2016 | Powell | A61K 35/17 |
| 11,104,732 B2* | 8/2021 | Cao | C07K 14/70585 |
| 2016/0185861 A1* | 6/2016 | Bedoya | A61K 35/17 |
| | | | 435/465 |
| 2016/0280798 A1* | 9/2016 | Orentas | A61K 35/17 |
| 2016/0340406 A1* | 11/2016 | Zhao | C07K 14/70596 |
| 2018/0066037 A1* | 3/2018 | Jin | C12N 5/0636 |
| 2018/0311374 A1* | 11/2018 | Lobb | A61K 9/0019 |
| 2018/0353545 A1* | 12/2018 | Webster | C07D 471/04 |
| 2019/0038671 A1* | 2/2019 | Fan | C07K 16/2818 |
| 2020/0002402 A1* | 1/2020 | Emtage | C07K 14/70578 |
| 2020/0030381 A1* | 1/2020 | Bolen | C07K 14/705 |
| 2020/0069732 A1* | 3/2020 | Cao | A61K 35/17 |
| 2020/0172865 A1* | 6/2020 | Pu | A61K 35/17 |
| 2020/0181269 A1* | 6/2020 | Qi | C12N 7/00 |
| 2020/0262891 A1* | 8/2020 | Mukherjee | C07K 14/70596 |
| 2020/0352996 A1* | 11/2020 | Hu | C07K 14/7051 |
| 2021/0017248 A1* | 1/2021 | Bluestone | A61P 35/00 |
| 2021/0024890 A1* | 1/2021 | Pu | C12N 5/0636 |
| 2021/0060069 A1* | 3/2021 | Xiao | A61K 38/204 |
| 2021/0077528 A1* | 3/2021 | Cao | A61K 35/17 |
| 2021/0100841 A1* | 4/2021 | Xiao | C07K 16/3092 |
| 2021/0122802 A1* | 4/2021 | Pu | C07K 14/7051 |
| 2021/0252059 A1* | 8/2021 | Pu | A61K 39/001112 |
| 2021/0347893 A1* | 11/2021 | Cao | C07K 14/715 |
| 2022/0000921 A1* | 1/2022 | Xiao | A61K 39/001112 |
| 2022/0105134 A1* | 4/2022 | Cao | A61K 35/17 |

OTHER PUBLICATIONS

Long et al. (2015) Nature Medicine 21(6): 581-590.*
Golubovskaya et al. (2018) Frontiers in Bioscience, Landmark; 23: 2245-2254, (Jun. 1, 2018).*

* cited by examiner

*Primary Examiner* — Ilia I Ouspenski
(74) *Attorney, Agent, or Firm* — Lee & Hayes, P.C.

(57) ABSTRACT

The present disclosure relates to compositions and methods for enhancing CAR T therapy through uses of co-stimulation. Some embodiments relate to an isolated nucleic acid sequence encoding a chimeric antigen receptor (CAR) and an agent associated with a co-stimulatory molecule, the CAR comprising an intracellular domain of a costimulatory molecule.

9 Claims, 13 Drawing Sheets
Specification includes a Sequence Listing.

FIG. 3

| Structure of isolated nucleic acid sequence | SEQ ID NO: |
|---|---|
| 41BBCAR-IRES-ICOSL | 1-2-3-5-4 & 10 |
| 41BBCAR-IRES-GITRL | 1-2-3-5-4 & 8 |
| ICOSCAR-IRES-41BBL | 1-2-9-4 & 6 |
| ICOSCAR-IRES-GITRL | 1-2-9-4 & 8 |
| GITRCAR-IRES-41BBL | 1-2-3-7-4 & 6 |
| GITRCAR-IRES-ICOSL | 1-2-3-7-4 & 10 |

CAR T THERAPY THROUGH USES OF CO-STIMULATION

CROSS REFERENCE TO RELATED PATENT APPLICATIONS

This application claims the benefit of U.S. Provisional Application 62/725,967, filed on Aug. 31, 2018, which is hereby incorporated by reference in its entirety.

SEQUENCE LISTING INFORMATION

A computer readable textfile, entitled "Sequence listing_ST25-2.txt," created on or about Sep. 26, 2019, with a file size of about 92 KB, contains the sequence listing for this application and is hereby incorporated by reference in its entirety.

TECHNICAL FIELD

The present disclosure relates to compositions and methods for expanding and maintaining modified cells including genetically modified cells, and uses thereof in the treatment of diseases, including cancer.

BACKGROUND

T cells genetically targeted to certain malignancies have demonstrated tremendous clinical outcomes. However, until recently, the use of CAR T-cell therapy has been restricted to small clinical trials, largely in patients with advanced blood cancers. Conventional design of CAR and CAR-based therapy seem not to be able to activate CAR T cells and/or kill solid tumor. While multiple co-stimulatory domains may be combined, activation of T cells and killing functions of the T cells are still not ideal for treating solid tumor.

SUMMARY

Embodiments here relate to compositions and methods for treating cancer using CAR Cell. Some embodiments relate to an isolated nucleic acid sequence encoding a chimeric antigen receptor (CAR) and an agent associated with a co-stimulatory molecule, the CAR comprising an intracellular domain of a costimulatory molecule. Some embodiments relate to an isolated cell comprising a CAR and an agent associated with a co-stimulatory molecule, the CAR comprising an intracellular domain of a costimulatory molecule. In some embodiments, the agent is located on the surface of the cell.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 3 is a schematic diagram illustrating examples of structures of isolated nucleic acid sequences.

DETAILED DESCRIPTION

Figure 1:
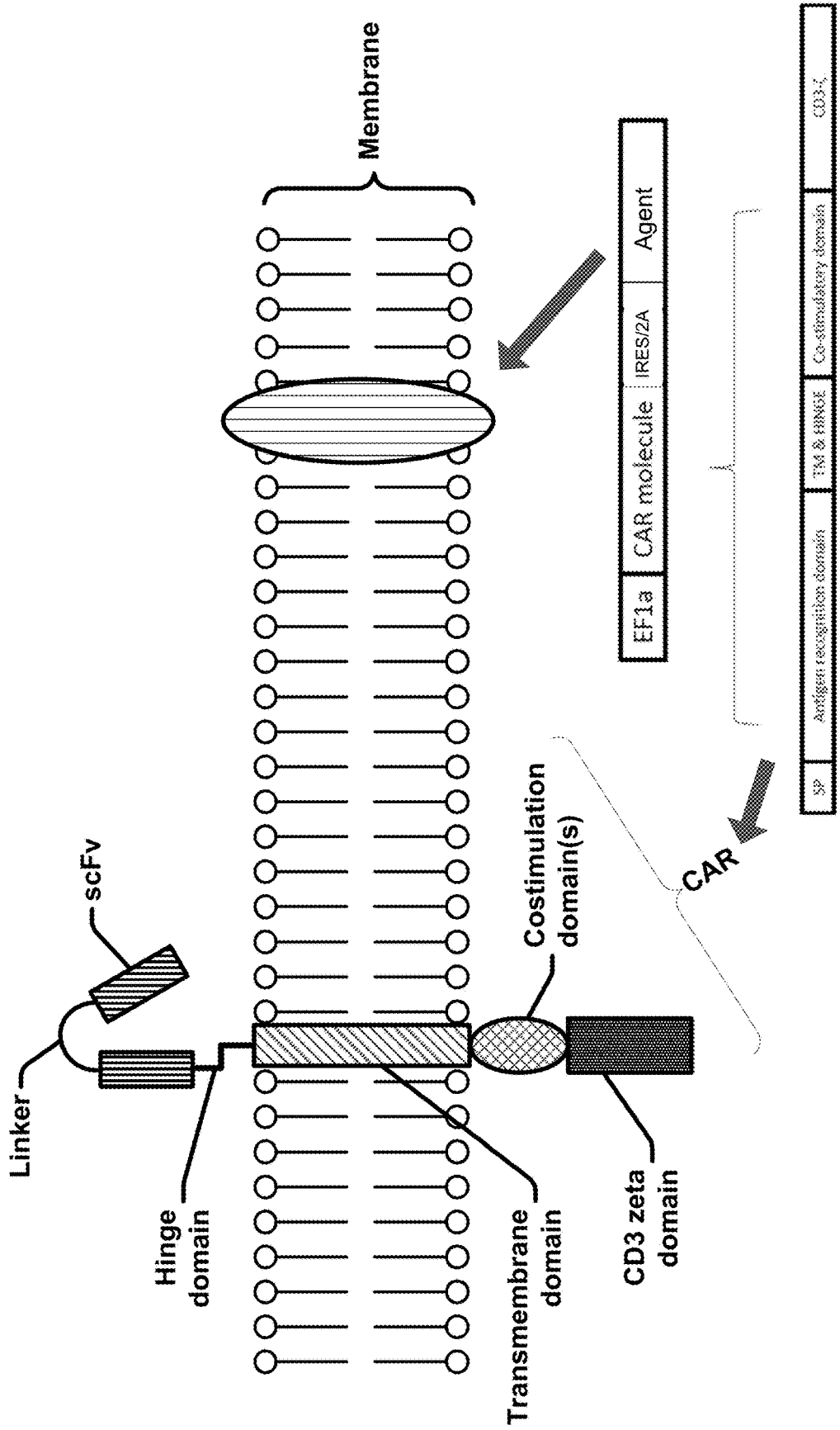
FIG. 1 is a schematic diagram illustrating an example of a CAR structure.
Figure 2:
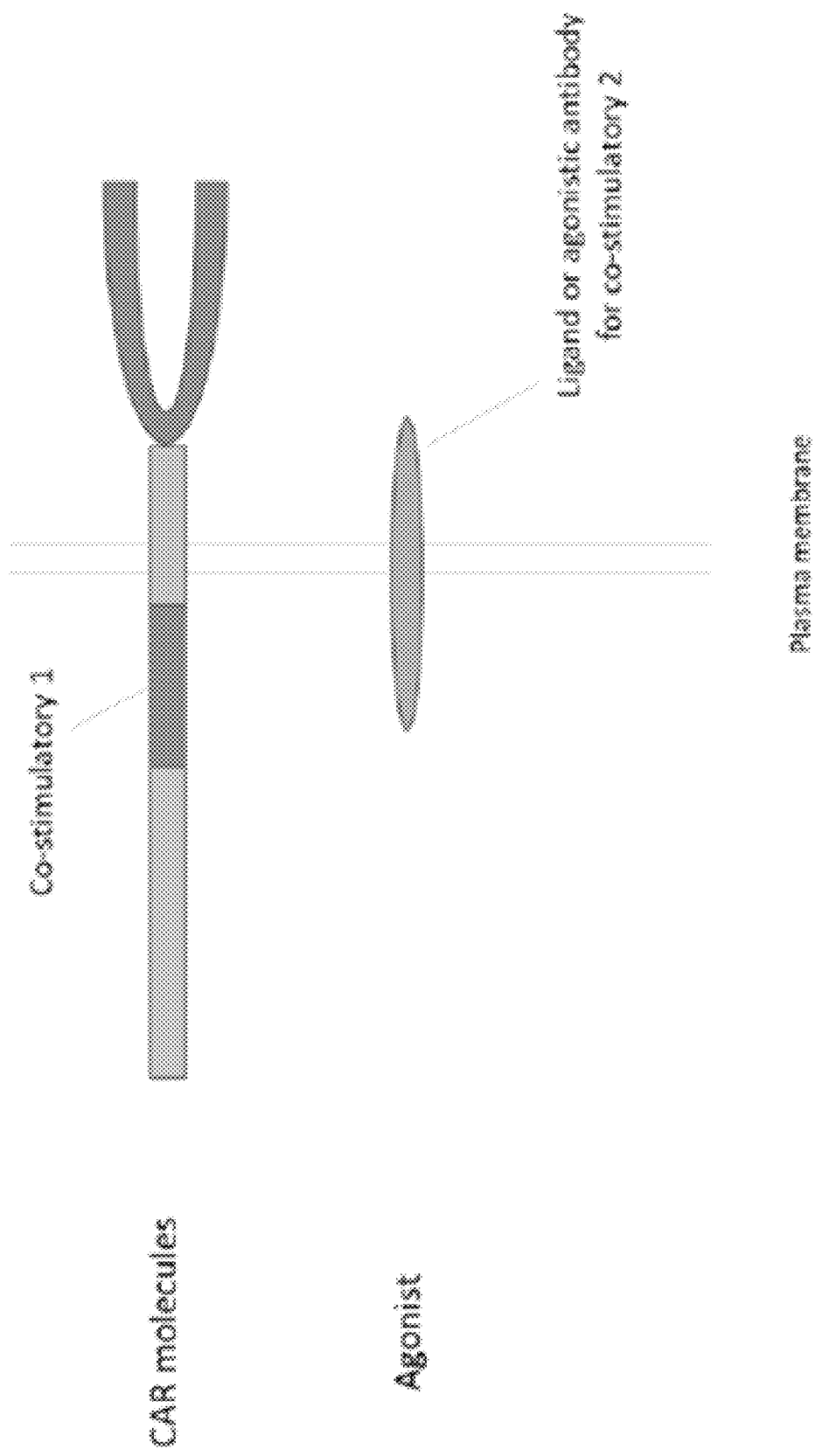
FIG. 2 is a schematic diagram illustrating an example of a portion of a cell containing a CAR.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab')$_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', F(ab')$_2$, and Fv fragments;

diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. κ and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated to the recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

In embodiments, viruses are used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

In embodiments, non-viral methods are used for delivering nucleic acids into a cell. Examples of non-viral methods include electroporation, gene gun, sonoporation, magnetofection, and the use of oligonucleotides, lipoplexes, dendrimers, and inorganic nanoparticles. The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid | Disease tumor | Solid Tumor | Disease tumor |
|---|---|---|---|
| PRLR | Breast Cancer | MUC21 | Esophageal cancer |
| CLCA1 | colorectal Cancer | MUC16 | Ovarian cancer |
| MUC12 | colorectal Cancer | MS4A12 | Colorectal cancer |
| GUCY2C | colorectal Cancer | ALPP | Endometrial cancer |
| GPR35 | colorectal Cancer | CEA | Colorectal carcinoma |
| CR1L | Gastric Cancer | EphA2 | Glioma |
| MUC 17 | Gastric Cancer | FAP | Mesotelioma |
| TMPRSS11 | esophageal Cancer | GPC3 | Lung squamous cell |
| MUC21 | esophageal Cancer | 1L13-Rα2 | Glioma |
| TMPRSS11 | esophageal Cancer | Mesothelin | Metastatic cancer |
| CD207 | bladder Cancer | PSMA | Prostate cancer |
| SLC30A8 | pancreatic Cancer | | |
| CFC1 | pancreatic Cancer | ROR1 | Breast lung carcinoma |
| SLC12A3 | Cervical Cancer | VEGFR-II | Metastatic cancer |
| SSTR1 | Cervical tumor | GD2 | Neuroblastoma |

TABLE 1-continued

| Solid | Disease tumor | Solid Tumor | Disease tumor |
|---|---|---|---|
| GPR27 | Ovary tumor | FR-α | Ovarian carcinoma |
| FZD10 | Ovary tumor | ErbB2 | Carcinomasb |
| TSHR | Thyroid Tumor | EpCAM | Carcinomasa |
| SIGLEC15 | Urothelial cancer | EGFRvIII | Glioma - Glioblastoma |
| SLC6A3 | Renal cancer | EGFR | Glioma - NSCL cancer |
| KISS1R | Renal cancer | tMUC 1 | Cholangiocarcinoma, |
| QRFPR | Renal cancer: | PSCA | pancreas, stomach, or |
| GPR119 | Pancreatic cancer | ADAM12 | Breast cancer, pancreatic |
| CLDN6 | Endometrial cancer/ | SLC45A3 | Prostate cancer |
| UPK2 | Urothelial cancer (including | ACPP | Prostate cancer |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human, or animal, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true.

If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-$\beta$, and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen presenting cell (e.g., an APC, a dendritic cell, a B-cell, and the like) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain and a cytoplasmic domain or intracellular domain. In embodiments, the domains of the CAR are on the same polypeptide chain, for example a chimeric fusion protein. In embodiments, the domains are on different polypeptide chains, for example the domains are not contiguous.

The extracellular domain of a CAR molecule includes an antigen binding domain. The antigen binding domain is for expanding and/or maintaining the modified cells, such as a CAR T cell or for killing a tumor cell, such as a solid tumor. In embodiments, the antigen binding domain for expanding and/or maintaining modified cells binds an antigen, for example, a cell surface molecule or marker, on the surface of a WBC. In embodiments, the WBC is a granulocyte, monocyte and or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

In embodiments, the antigen binding domain for killing a tumor, binds an antigen on the surface of a tumor, for example a tumor antigen or tumor marker. Tumor antigens are proteins that are produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), $\beta$-human chorionic gonadotropin, alphafetoprotein (AFP), lectin-reactive AFP, thyroglobulin, RAGE-1, MN- CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19CAR, which is a CAR molecule that includes a antigen binding domain that binds CD19.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS)$_3$ (SEQ ID NO: 31), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In embodiments, the signaling domain includes a CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

The present disclosure relate to a modified cell comprising a first nucleic acid encoding a chimeric antigen receptor (CAR) and a second nucleic acid encoding an agent associated with a first co-stimulatory molecule, wherein the CAR comprises an extracellular domain, a transmembrane domain, and an intracellular domain, the extracellular domain binds an antigen, and the intracellular domain comprises an intracellular domain of a second co-stimulatory molecule. In embodiments, the modified cell is a T cell, NK cell, or dendritic cell.

In embodiments, the agent is located on the surface of the cell. In embodiments, the agent is a co-stimulatory ligand or agonistic antibody of the first co-stimulatory molecule. An "agonist antibody," as used herein, is an antibody which activates a biological activity of the antigen it binds. In embodiments, agonist antibody activation, partial dissociation of antibodies allows the antigen-binding fragment (Fab) arms of a single antibody to interact with more than two receptors in a dynamic fashion, resulting in recruitment of multiple receptor monomers into a receptor oligomer where signaling activation can be triggered. In embodiments, antigen-presenting cells (APCs) acts as a scaffold to crosslink agonist antibody bound to a receptor (e.g., co-stimulatory receptor), leading to receptor supercluster formation and increased agonist signaling. Some proteins (such as the CD28 family and the TNF receptor family) have an agonist antibody for tumor therapy. More information about agonist antibodies and co-stimulatory molecules may be found at Nature Reviews Drug Discovery volume 17, pages 509-527 (2018), which is incorporated herein for a reference.

In embodiments, the agent comprises a ligand for B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds Toll ligand receptor, glucocorticoid-induced TNFR-related protein (GITR), or a ligand that specifically binds with B7-H3.

In embodiments, the agent comprises an agonistic antibody that specifically binds with a co-stimulatory molecule that is CD27, CD28, 4-1BB, OX40, CD30, CD40, PD-1, ICOS, lymphocyte function-associated antigen-1 (LFA-1), CD2, CD7, LIGHT, NKG2C, B7-H3 or comprises a ligand that specifically binds with CD83.

In embodiments, the second co-stimulatory molecule is selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, GITR, and any combination thereof.

In embodiments, the first co-stimulatory molecule is ICOS, and the second co-stimulatory molecule is 4-1BB, or the isolated nucleic acid sequence comprises the amino acid sequences of SEQ ID NOs: 1, 2, 3, 5, 4, and 10 in 5' to 3' order; the first co-stimulatory molecule is GITR, and the second co-stimulatory molecule is 4-1BB, or the isolated nucleic acid sequence comprises the amino acid sequences of SEQ ID NOs: 1, 2, 3, 5, 4, and 8 in 5' to 3' order; the first co-stimulatory molecule is 4-1BB, and the second co-stimulatory molecule is GITR, or the isolated nucleic acid sequence comprises the amino acid sequences of SEQ ID NOs: 1, 2, 3, 7, 4, and 6 in 5' to 3' order; the first co-stimulatory molecule is ICOS, and the second co-stimulatory molecule is GITR, or the isolated nucleic acid sequence comprises the amino acid sequences of SEQ ID NOs: 1, 2, 3, 7, 4, and 10 in 5' to 3' order; the first co-stimulatory molecule is 4-1BB, and the second co-stimulatory molecule is ICOS; or the isolated nucleic acid sequence comprises the amino acid sequences of SEQ ID NOs: 1, 2, 9, 4, and 6 in 5' to 3' order; or the first co-stimulatory molecule is GITR, and the second co-stimulatory molecule is ICOS, or the isolated nucleic acid sequence comprises the amino acid sequences of SEQ ID NOs: 1, 2, 9, 4, and 8 in 5' to 3' order.

In embodiments, the first co-stimulatory molecule is 4-1-BB, and the second co-stimulatory molecule is 4-1BB, CD86, GITR, or CD137. In embodiments, the CAR further comprises an antigen binding domain that binds to a tumor antigen, a transmembrane domain, and a CD3 zeta signaling domain. In embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE AI, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8.

Some embodiments relate to a modified cell comprising a first nucleic acid encoding a chimeric antigen receptor (CAR) and a second nucleic acid encoding an agent associated with a first co-stimulatory molecule, wherein the CAR comprises an intracellular domain of a second co-stimulatory molecule. In embodiments, the first and second co-stimulatory molecules are identical or different. In embodiments, the agent is located on the surface of the cell, and/or the agent is a co-stimulatory ligand or agonistic antibody of the first co-stimulatory molecule. In embodiments, the modified cell comprises a nucleic acid encoding at least one of the SEQ ID NO: 21-30.

Some embodiments relate to a composition comprising a population of the modified cell. Some embodiments relate to a method of enhancing T-cell response in a subject or treating a tumor of the subject, the method comprising: administering an effective amount of the composition.

In embodiments, the population of cells described herein is used in autologous CAR T cell therapy. In embodiments, the CAR T cell therapy is allogeneic CAR T cell therapy, TCR T cell therapy, and NK cell therapy.

The cells, including CAR cells and modified cells, described herein can be derived from a stem cell. The stem cells may be adult stem cells, embryonic stem cells, or non-human stem cells, cord blood stem cells, progenitor cells, bone marrow stem cells, induced pluripotent stem cells, totipotent stem cells, or hematopoietic stem cells. The cells can also be a dendritic cell, an NK-cell, a B-cell, or a T cell selected from the group consisting of inflammatory T lymphocytes, cytotoxic T lymphocytes, regulatory T lymphocytes, and helper T lymphocytes. In embodiments, the cells can be derived from the group consisting of CD4+T-lymphocytes and CD8+T-lymphocytes. Prior to expansion and genetic modification of the cells described herein, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art, can be used. In embodiments, the cells may be derived from a healthy donor, from a patient diagnosed with cancer or from a patient diagnosed with an infection. In embodiments, the cells are part of a mixed population of cells which present different phenotypic characteristics.

The term "stem cell" refers to any type of cell which has the capacity for self-renewal and the ability to differentiate into other kind(s) of cells. For example, a stem cell gives rise either to two daughter stem cells (as occurs in vitro with embryonic stem cells in culture) or to one stem cell and a cell that undergoes differentiation (as occurs, e.g. in hematopoietic stem cells, which give rise to blood cells). Different categories of stem cells may be distinguished on the basis of their origin and/or on the extent of their capacity for differentiation into other types of cell. Stem cells can include embryonic stem (ES) cells (i.e., pluripotent stem cells), somatic stem cells, induced pluripotent stem cells, and any other types stem cells.

Pluripotent embryonic stem cells can be found in the inner cell mass of a blastocyst and have high innate capacity for differentiation. For example, pluripotent embryonic stem cells have the potential to form any type of cell in the body. When grown in vitro for long periods of time, ES cells maintain pluripotency, and progeny cells retain the potential for multilineage differentiation.

Somatic stem cells can include fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited number of different types of cells and have been described as multipotent. "Tissue-specific" stem cells normally give rise to only one type of cell. For example, embryonic stem cells can differentiate into blood stem cells (e.g., Hematopoietic stem cells (HSCs)), which can further differentiate into various blood cells (e.g., red blood cells, platelets, white blood cells, etc.).

Induced pluripotent stem cells (iPS cells or iPSCs) can include a type of pluripotent stem cell artificially derived from a non-pluripotent cell (e.g., an adult somatic cell) by inducing expression of specific genes. Induced pluripotent stem cells are similar to naturally occurring pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be isolated from adult stomach, liver, skin cells, and blood cells.

In embodiments, the CAR cells, the modified cell, or the cell is a T cell, an NK cell, a macrophage or a dendritic cell. For example, the CAR cells, the modified cell, or the cell is a T cell.

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further, since an antibody has two heavy chains and two light chains, an antibody has twelve CDRs altogether for binding antigens. In embodiments, the CAR molecules comprise one or more CDRs for binding HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8.

Some embodiments relate to a modified cell comprising nucleic acids encoding a first co-stimulatory molecule and a second co-stimulatory molecule. In embodiments, the first nucleic acid encodes a chimeric antigen receptor (CAR), and a second nucleic acid encodes an agent associated with a first co-stimulatory molecule, wherein the CAR comprises an extracellular domain, a transmembrane domain, and an intracellular domain, the extracellular domain binds an antigen, and the intracellular domain comprises an intracellular domain of a second co-stimulatory molecule. In embodiments, the modified cell is a T cell, NK cell, or dendritic cell.

Some embodiments relate to composition comprising a population of the modified cell. Some embodiments relate to a method of enhancing T cell response in a subject or treating a tumor of the subject, the method comprising: administering an effective amount of the composition.

In embodiments, the agent is located on the surface of the cell. In embodiments, the agent is a co-stimulatory ligand or agonistic antibody of the first co-stimulatory molecule.

In embodiments, comprises a ligand for B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds Toll ligand receptor, TNFR-related protein (GITR), or a ligand that specifically binds with B7-H3. In embodiments, the agent comprises an agonistic antibody that specifically binds a co-stimulatory molecule comprising CD27, CD28, 4-1BB, OX40, CD30, CD40, PD-1, 1005, lymphocyte function-associated antigen-1 (LFA-1), CD2, CD7, LIGHT, NKG2C, B7-H3 or wherein the agent comprises a ligand that specifically binds CD83. 6. The modified cell of claim 1, wherein the second co-stimulatory molecule is selected from the group consisting of CD27, CD28, 4-1BB, OX40, CD30, CD40, PD-1, 1005, lymphocyte function-associated antigen-1 (LFA-1), CD2, CD7, LIGHT, NKG2C, B7-H3, GITR, and any combination thereof.

In embodiments, the first co-stimulatory molecule is ICOS, and the second co-stimulatory molecule is 4-1BB, or the isolated nucleic acid sequence comprises the amino acid sequences of SEQ ID NOs: 1, 2, 3, 5, 4, and 10 in 5' to 3' order; the first co-stimulatory molecule is GITR, and the second co-stimulatory molecule is 4-1BB, or the isolated nucleic acid sequence comprises the amino acid sequences of SEQ ID NOs: 1, 2, 3, 5, 4, and 8 in 5' to 3' order; the first co-stimulatory molecule is 4-1BB, and the second co-stimulatory molecule is GITR, or the isolated nucleic acid sequence comprises the amino acid sequences of SEQ ID NOs: 1, 2, 3, 7, 4, and 6 in 5' to 3' order; the first co-stimulatory molecule is ICOS, and the second co-stimulatory molecule is GITR, or the isolated nucleic acid sequence comprises the amino acid sequences of SEQ ID NOs: 1, 2, 3, 7, 4, and 10 in 5' to 3' order; the first co-stimulatory molecule is 4-1BB, and the second co-stimulatory molecule is ICOS; or the isolated nucleic acid sequence comprises the amino acid sequences of SEQ ID NOs: 1, 2, 9, 4, and 6 in 5' to 3' order; or the first co-stimulatory molecule is GITR, and the second co-stimulatory molecule is ICOS, or the isolated nucleic acid sequence comprises the amino acid sequences of SEQ ID NOs: 1, 2, 9, 4, and 8 in 5' to 3' order.

In embodiments, the first co-stimulatory molecule is 4-1-BB, and the second co-stimulatory molecule is 4-1BB, CD86, GITR, or CD137. In embodiments, the CAR further comprises an antigen binding domain that binds a tumor antigen, a transmembrane domain, and a CD3 zeta signaling domain. In embodiments, the tumor antigen comprises HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8.

Some embodiments relate to a polynucleotide encoding the CAR and/or the agent described above. Some embodiments relate to a method or use of polynucleotide. The method or use includes: providing a viral particle (e.g., AAV or its variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719, which is incorporated herein by reference.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. An isolated nucleic acid sequence encoding a chimeric antigen receptor (CAR) and an agent associated with a first co-stimulatory molecule, the CAR comprising an intracellular domain of a second costimulatory molecule.
2. An isolated cell comprising a CAR and an agent associated with a first co-stimulatory molecule, the CAR comprising an intracellular domain of a second costimulatory molecule.
3. The isolated cell of embodiment 2, wherein the agent is located on the surface of the cell.
4. The isolated nucleic acid sequence or cell of any one of embodiments 1-3, wherein the agent is a co-stimulatory ligand of the first co-stimulatory molecule.
5. The isolated nucleic acid sequence or cell of any one of embodiments 1-3, wherein the agent comprises a ligand for B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds Toll ligand receptor, TNFR-related protein (GITR), or a ligand that specifically binds with B7-H3.

6. The isolated nucleic acid sequence or cell of any one of embodiments 1-3, wherein the agent comprises an antibody that specifically binds with a co-stimulatory molecule that is CD27, CD28, 4-1BB, OX40, CD30, CD40, PD-1, ICOS, lymphocyte function-associated antigen-1 (LFA-1), CD2, CD7, LIGHT, NKG2C, B7-H3 or comprises a ligand that specifically binds with CD83.

7. The isolated nucleic acid sequence or cell of any one of embodiments 1-3, wherein the second co-stimulatory molecule is selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, GITR, and any combination thereof.

8. The isolated nucleic acid sequence or cell of any one of embodiments 1-3, wherein the first co-stimulatory molecule is ICOS, and the second co-stimulatory molecule is 4-1BB.

9. The isolated nucleic acid sequence or cell of embodiment 8, wherein the isolated nucleic acid sequence comprises the amino acid sequences of SEQ ID NOs: 1, 2, 3, 5, 4, and 10 in 5' to 3' order.

10. The isolated nucleic acid sequence or cell of any one of embodiments 1-3, wherein the first co-stimulatory molecule is GITR, and the second co-stimulatory molecule is 4-1BB.

11. The isolated nucleic acid sequence or cell of embodiment 10, wherein the isolated nucleic acid sequence comprises the amino acid sequences of SEQ ID NOs: 1, 2, 3, 5, 4, and 8 in 5' to 3' order.

12. The isolated nucleic acid sequence or cell of any one of embodiments 1-3, wherein the first co-stimulatory molecule is 4-1BB, and the second co-stimulatory molecule is GITR.

13. The isolated nucleic acid sequence or cell of embodiment 12, wherein the isolated nucleic acid sequence comprises the amino acid sequences of SEQ ID NOs: 1, 2, 3, 7, 4, and 6 in 5' to 3' order.

14. The isolated nucleic acid sequence or cell of any one of embodiments 1-3, wherein the first co-stimulatory molecule is ICOS, and the second co-stimulatory molecule is GITR.

15. The isolated nucleic acid sequence or cell of embodiment 14, wherein the isolated nucleic acid sequence comprises the amino acid sequences of SEQ ID NOs: 1, 2, 3, 7, 4, and 10 in 5' to 3' order.

16. The isolated nucleic acid sequence or cell of any one of embodiments 1-3, wherein the first co-stimulatory molecule is 4-1BB, and the second co-stimulatory molecule is ICOS.

17. The isolated nucleic acid sequence or cell of embodiment 16, wherein the isolated nucleic acid sequence comprises the amino acid sequences of SEQ ID NOs: 1, 2, 9, 4, and 6 in 5' to 3' order.

18. The isolated nucleic acid sequence or cell of any one of embodiments 1-3, wherein the first co-stimulatory molecule is GITR, and the second co-stimulatory molecule is ICOS.

19. The isolated nucleic acid sequence or cell of embodiment 18, wherein the isolated nucleic acid sequence comprises the amino acid sequences of SEQ ID NOs: 1, 2, 9, 4, and 8 in 5' to 3' order.

20. The isolated nucleic acid sequence or cell of any one of embodiments 1-3, wherein the CAR further comprises an antigen binding domain that binds a tumor antigen, a transmembrane domain, and a CD3 zeta signaling domain.

21. The isolated nucleic acid sequence or cell of embodiment 20, wherein the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8.

22. The isolated nucleic acid sequence or cell of embodiment 20, wherein the antigen binding domain comprises the amino acid sequence of one of SEQ ID NOS: 2 and 11-20.

23. A vector comprising the isolated nucleic acid sequence of embodiment 1.

24. An isolated cell comprising the isolated nucleic acid sequence of embodiment 1.

25. The isolated cell of any embodiments 2, 3, and 16, wherein the cell is a T cell, NK cell, or dendritic cell.

26. A composition comprising a population of the isolated cell of embodiment 17.

27. A method of enhancing T-cell response in a subject or treating a tumor of the subject, the method comprising: administering an effective amount of the composition of embodiment 18.

28. The method of embodiment 26, wherein the isolated cell is a T cell.

29. A modified cell comprising a first nucleic acid encoding a chimeric antigen receptor (CAR) and a second nucleic acid encoding an agent associated with a first co-stimulatory molecule, wherein the CAR comprises an intracellular domain of a second co-stimulatory molecule.

30. The modified cell of embodiment 29, wherein the first and second co-stimulatory molecules are identical or different.

31. The modified cell of embodiment 29, wherein the agent is located on the surface of the cell, and/or the agent is a co-stimulatory ligand or agonistic antibody of the first co-stimulatory molecule.

32. The modified cell of one of embodiments 29-31, wherein the agent comprises a ligand for B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds Toll ligand receptor, TNFR-related protein (GITR), or a ligand that specifically binds with B7-H3.

33. The modified cell of one of embodiments 29-31, wherein the agent comprises an agonistic antibody that specifically binds with a co-stimulatory molecule that is CD27, CD28, 4-1BB, OX40, CD30, CD40, PD-1, ICOS, lymphocyte function-associated antigen-1 (LFA-1), CD2, CD7, LIGHT, NKG2C, B7-H3 or comprises a ligand that specifically binds with CD83.

34. The modified cell of one of embodiments 29-33, wherein the second co-stimulatory molecule is selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, GITR, and any combination thereof.

35. The modified cell of one of embodiments 29-34, wherein: the first co-stimulatory molecule is ICOS, and the second co-stimulatory molecule is 4-1BB, or the isolated nucleic acid sequence comprises the amino acid sequences of SEQ ID NOs: 1, 2, 3, 5, 4, and 10 in 5' to 3' order; the first co-stimulatory molecule is GITR, and the second co-stimulatory molecule is 4-1BB, or the isolated nucleic acid sequence comprises the amino acid sequences of SEQ ID NOs: 1, 2, 3, 5, 4, and 8 in 5' to 3' order; the first co-stimulatory molecule is 4-1BB, and the second co-stimulatory molecule is GITR, or the isolated nucleic acid sequence comprises the amino acid sequences of SEQ ID NOs: 1, 2, 3, 7, 4, and 6 in 5' to 3' order; the first co-stimulatory molecule is ICOS, and the second co-stimulatory molecule is GITR, or the isolated nucleic acid sequence comprises the amino acid sequences of SEQ ID NOs: 1, 2, 3, 7, 4, and 10 in 5' to 3' order; the first co-stimulatory molecule is 4-1BB, and the second co-stimulatory molecule is ICOS; or the isolated nucleic acid sequence comprises the amino acid sequences of SEQ ID NOs: 1, 2, 9, 4, and 6 in 5' to 3' order; or the first co-stimulatory molecule is GITR, and the second co-stimulatory molecule is ICOS, or the isolated nucleic acid sequence comprises the amino acid sequences of SEQ ID NOs: 1, 2, 9, 4, and 8 in 5' to 3' order.

36. The modified cell of one of embodiments 29-35, wherein the first co-stimulatory molecule is 4-1-BB, and the second co-stimulatory molecule is 4-1BB, CD86, GITR, or CD137.

37. The modified cell of one of embodiments 29-36, wherein the CAR further comprises an antigen binding domain that binds a tumor antigen, a transmembrane domain, and a CD3 zeta signaling domain.

38. The modified cell of embodiment 36, wherein the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8.

39. The modified cell of one of embodiments 29-11, wherein the modified cell is a T cell, NK cell, or dendritic cell.

40. A composition comprising a population of the modified cell of embodiment 10.

41. A method of enhancing T cell response in a subject or treating a tumor of the subject, the method comprising: administering an effective amount of the composition of embodiment 11.

42. A polynucleotide encoding the CAR and the agent of one of embodiments 29-39.

EXAMPLES

Example 1

CD3+ cells were obtained from a volunteer. The cells were transfected with various vectors encoding hCD19CAR, hCD19CAR-CD80, hCD19CAR-CD86, hCD19CAR-41BBL, and hCD19CAR-GITRL, respectively (hCD19CAR MOI 5:1; other vectors MOI: 10:1). The media were changed, and cells were expanded from day 2 to 5. CAR T cells were co-cultured with substrate cells to detect phenotype and cytokine release. The supernatant was collected, and copy numbers of CARs were measured. On day 8, cultured cells were collected and divided into groups, each including 200×10$^5$ cells. The cells were lysed, and the genomic DNA of the cells was extracted. The copy number of the cells was detected using 41 bb primers and probes. The data show that there is no significant difference in the copy numbers/per cell of each group.

TABLE 2

| | Total CAR copy/ug DNA | CAR % | CAR copy/CART cell |
|---|---|---|---|
| NT | N/A | 0 | N/A |
| hCD19CAR | 56176 | 33.6 | 1.044 |
| hCD19CAR-CD80 | 6790 | 5.91 | 0.718 |
| hCD19CAR-CD86 | 19679 | 11.9 | 1.033 |
| hCD19CAR-41BBL | 27667 | 15.87 | 1.089 |
| hCD19CAR-GITRL | 13120 | 11.34 | 0.723 |

Example 2

Figure 4:
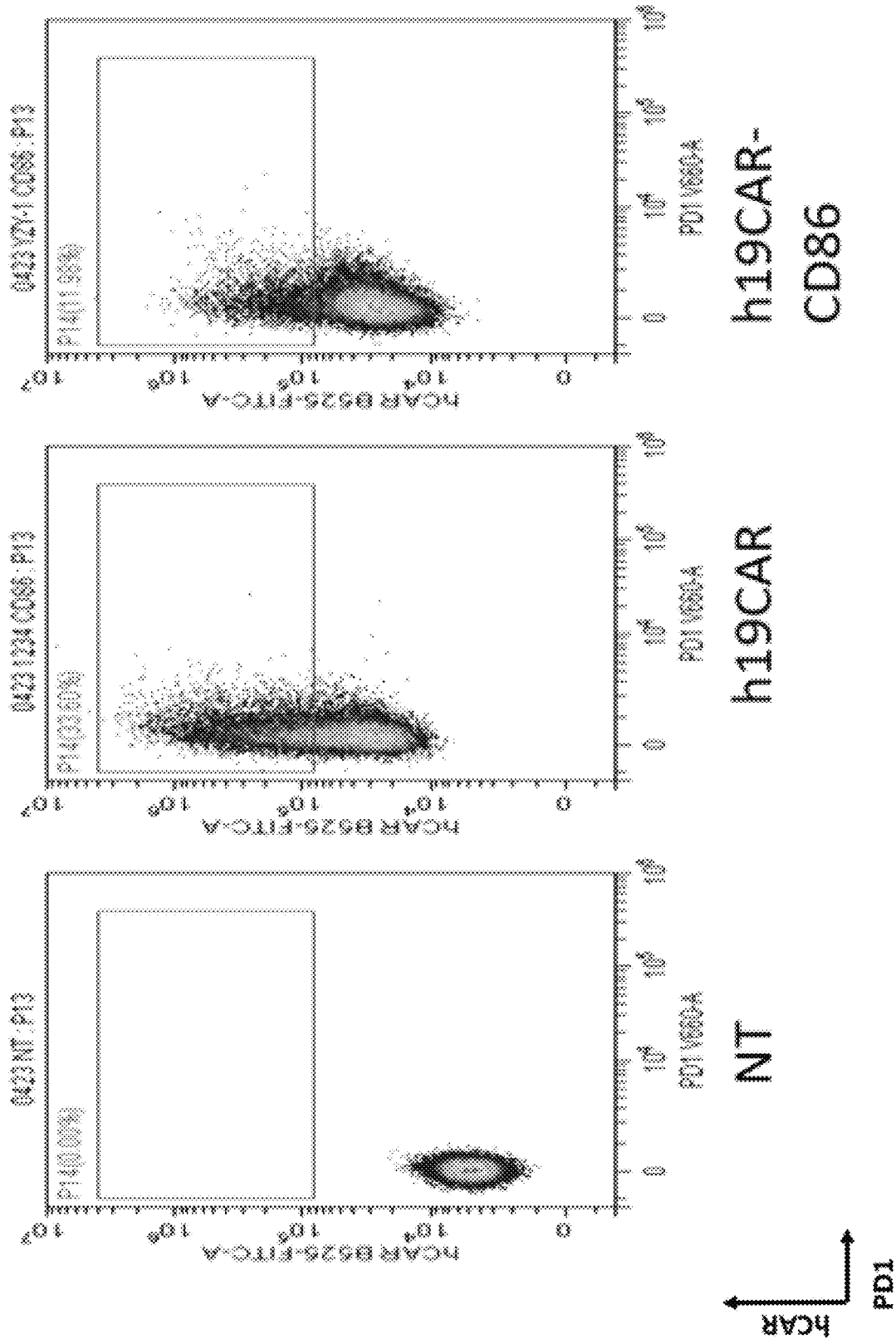
FIGS. 4 and 5 are results of the flow cytometry assay showing the expression intensity and expression level of CARs in various CAR T cells.
Figure 5:
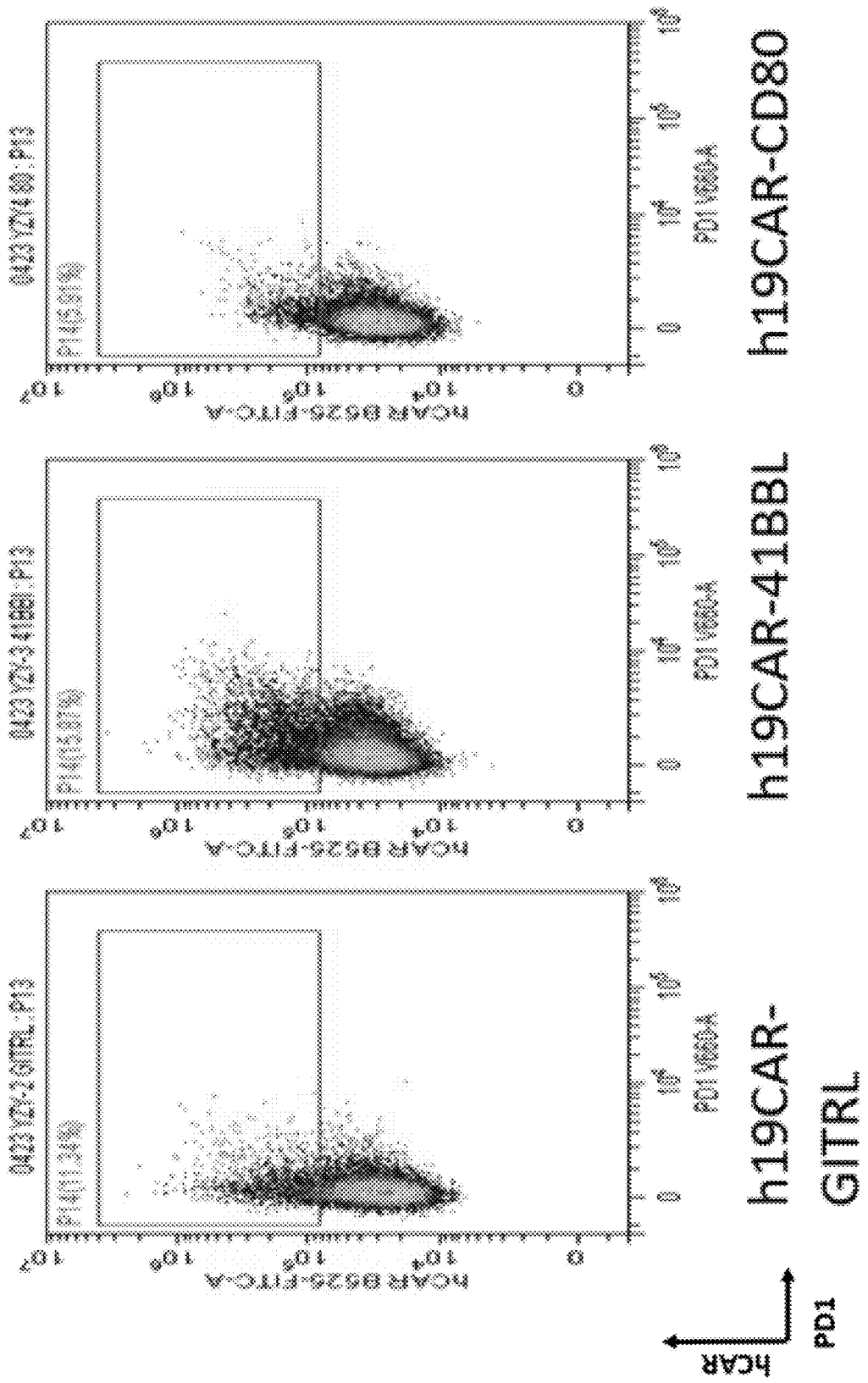

FIGS. 4 and 5 provide the results of the flow cytometry assay which show the expression intensity and expression level of CARs in various CAR T cells. On day 0, peripheral blood of healthy volunteers was taken, CD3+ T cells were sorted, and CD3/CD28 Dynabeads were added in a 1:1 ratio. On Day 2, T cells were transfected using lentivirus including various following vectors. CD19CAR was infected according to the infection ratio of MOI=10-1, while hCD19CAR, hCD19CAR-CD86, hCD19CAR-GITRUhCD19CAR-41BBL, hCD19CAR-CD80 infected cells according to the infection ratio of MOI=60:1. On Day 3, cell culture media were changed, the lentivirus was removed, and the cells were resuspended in a fresh medium. On Day 7, flow cytometry assays were used to detect CAR expression. CD19CAR is a humanized antibody and is therefore detected with a human CAR antibody. Flow cytometry was performed using human CAR antibody to detect the expression intensity and expression level of CARs.

Example 3

Figure 6:
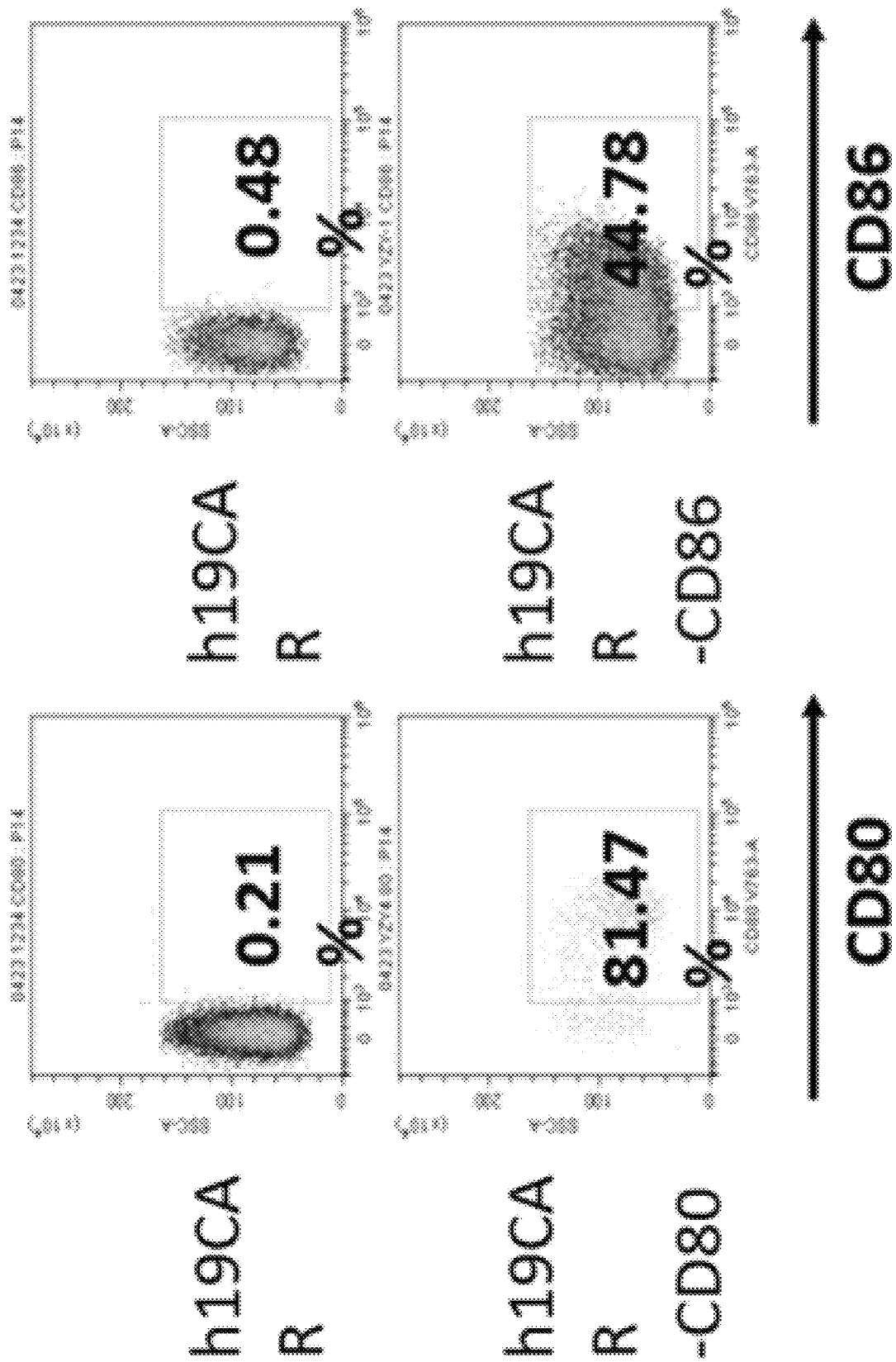
FIGS. 6 and 7 are results of the flow cytometry assay showing the expression intensity and expression level of ligands in various CAR T cells.
Figure 7:
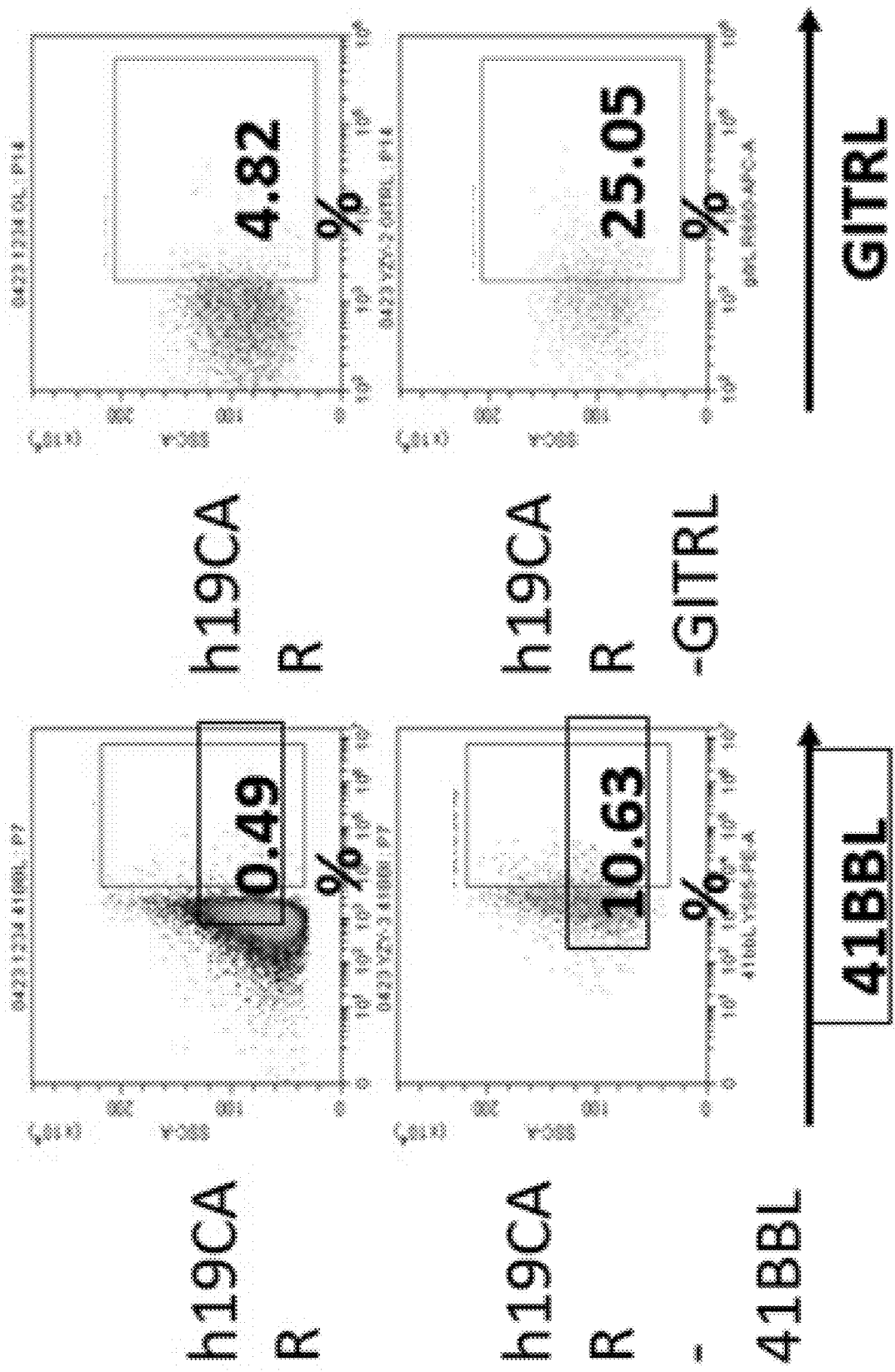

FIGS. 6 and 7 provide the results of the flow cytometry assay which show the expression intensity and expression level of ligands in various CAR T cells. On day 0, peripheral blood of healthy volunteers was taken, CD3+ T cells were sorted, and CD3/CD28 Dynabeads were added in a 1:1 ratio. On Day 2, T cells were transfected with lentivirus including various following vectors: CD19CAR infected according to the infection ratio of MOI=10:1, while hCD19CAR, hCD19CAR-CD86, hCD19CAR-GITRUhCD19CAR-41BBL, hCD19CAR-CD80 infected according to the infection ratio of MOI=60:1. On Day 3, the media were changed, the lentivirus was removed, and the cells were resuspended in fresh medium. On Day 7, flow cytometry assays were used to detect CAR and ligand expression. The data shows that each ligand is expressed and detected. Flow cytometry was performed using human CD80/86/41BBL/GITRL antibodies to detect the expression intensity and expression level of ligands.

Example 4

Figure 8:
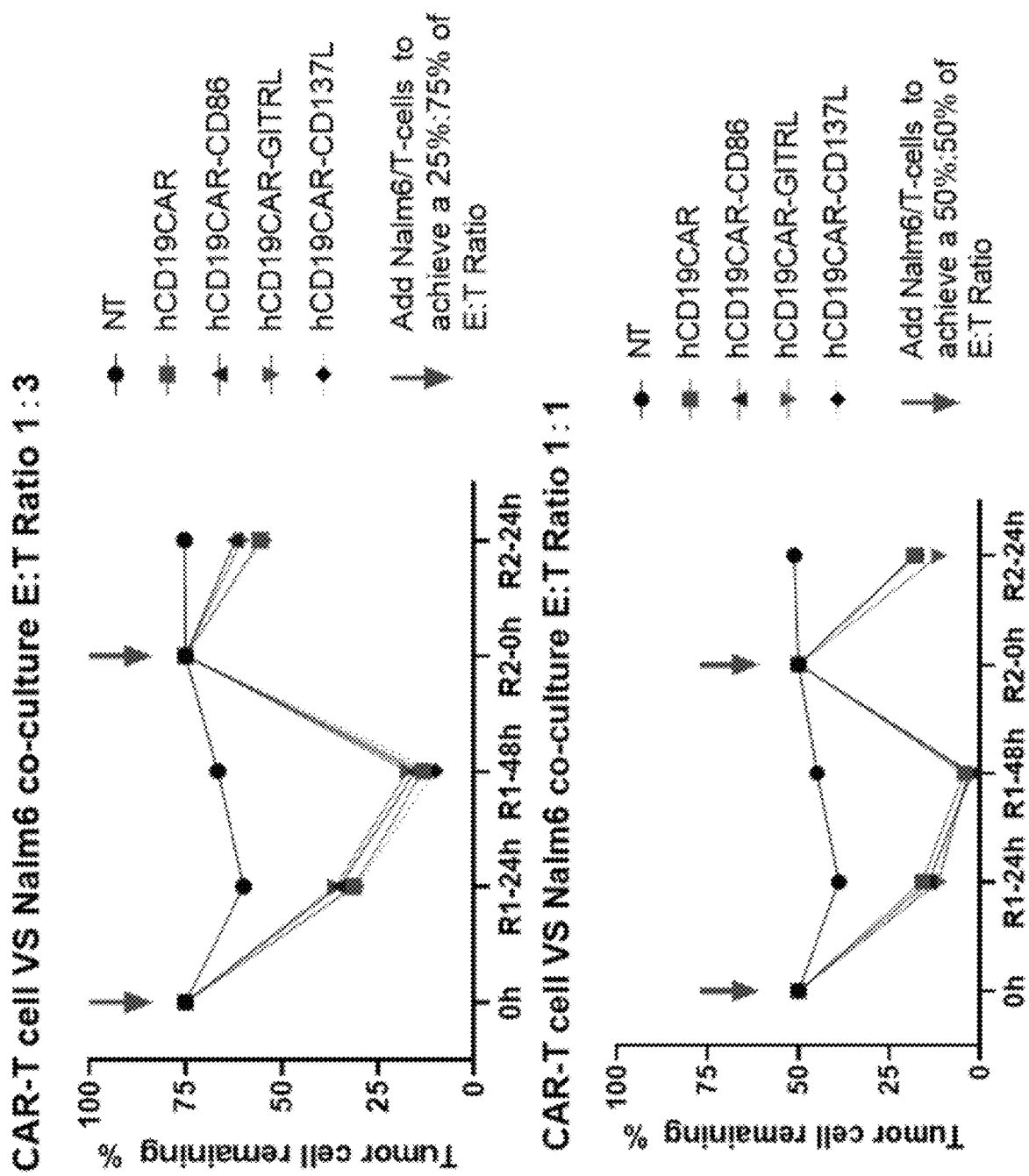
FIG. 8 shows the results of a killing function assay of various CAR T cells.

FIG. 8 shows the results of a killing function assay of various CAR T cells. Cells cultured to Day8 were leveled with NT cells using NT cells. 3×10$^4$ CAR+ cells were co-cultured with 10e4 Nalm-6 cells and 90e4 Nalm-6 cells, respectively. The residual of nalm6 cells was measured after tow replenishments of tumor. After hCD19CAR, hCD19CAR-CD86, hCD19CAR-GITRL, hCD19CAR-41BBL, hCD19CAR-CD80 T cells were co-cultured with nalm6 cells, respectively.

Example 5

Figure 9:
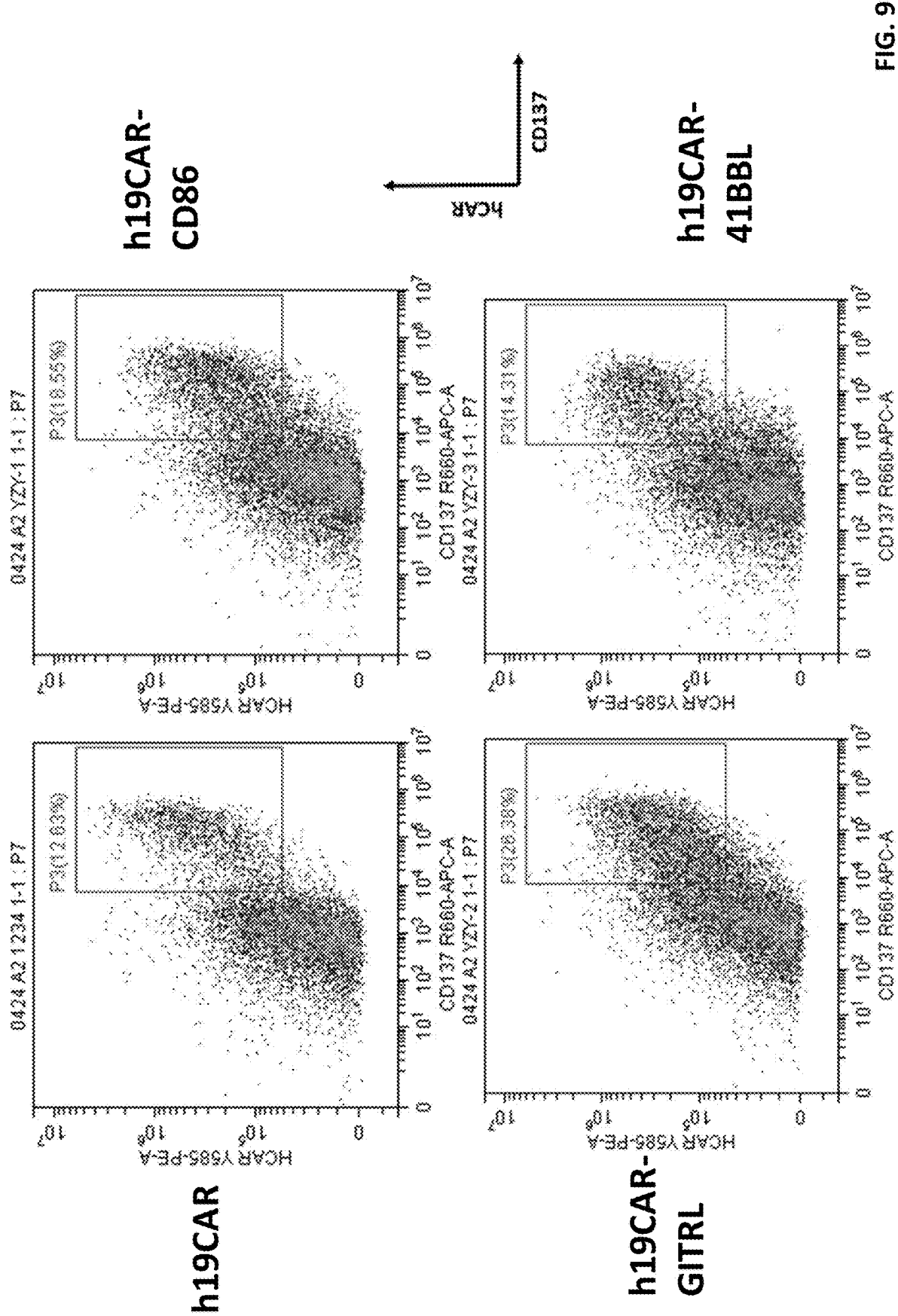
FIG. 9 is the results of cytometry assays showing activation marker expression in various CAR T cells.

FIG. 9 provides the results of cytometry assays which show activation marker expression in various CAR T cells. Cells were cultured to day 8, and then hCD19CAR, hCD19CAR-CD86, hCD19CAR-GITRL, hCD19CAR-41BBL, and hCD19CAR-CD80 CAR ratios were leveled using NT cells. $3\times10^4$ CAR+ cells were co-cultured with $1\times10^4$ Nalm-6 cells and $9\times10^4$ Nalm-6 cells, respectively. The activation of CAR-T cells was measured in 24 hours. It can be seen that the expression of CD137 in h19CAR-GITRL was significantly higher than that in other groups, indicating that the degree of its activation was significantly higher than other groups and demonstrating that GITRL helped CART cells with their activation functions during the killing process. When CAR-T cells are activated by tumor antigens, T cells up-regulate the expression of activated protein markers. The higher the expression and intensity, the higher the activation of CAR T cells.

Example 6

Figure 10:
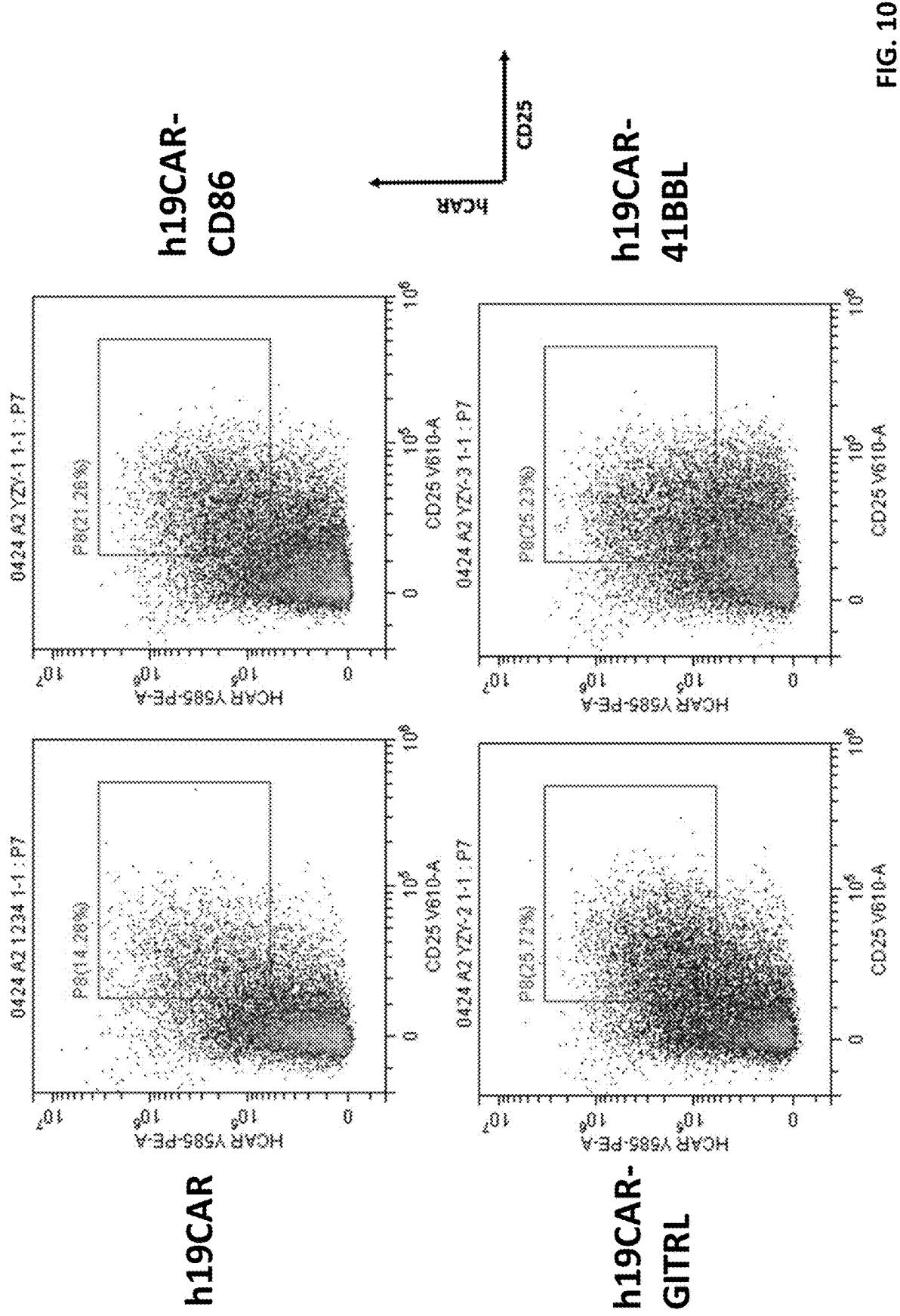
FIG. 10 is other results of cytometry assays showing activation marker expression in various CAR T cells.

FIG. 10 provides results of cytometry assays which show activation marker expression in various CAR T cells. Cells were cultured to day 8, and then hCD19CAR, hCD19CAR-CD86, hCD19CAR-GITRL, hCD19CAR-41BBL, and hCD19CAR-CD80 CAR ratios were leveled using NT cells. $3\times10^4$ CAR+ cells were co-cultured with 10e4 Nalm-6 cells and $9\times10^4$ Nalm-6 cells, respectively. The expression of CD25 in CAR-T cells was used to determine the activation of CAR T cells after 24 hours. The figure shows the expression level of CD25 was measured in hCD19CAR, hCD19CAR-CD86, hCD19CAR-GITRL, hCD19CAR-41BBL, hCD19CAR-CD80 T cells co-cultured with nalm6 cells, respectively. It can be seen that the expression of CD25 of h19CAR-GITRL was significantly higher than that of other groups, indicating that the degree of activation is significantly higher than in other groups and demonstrating that GITRL helped CART cells with their activation during the killing process.

Example 7

Figure 11:
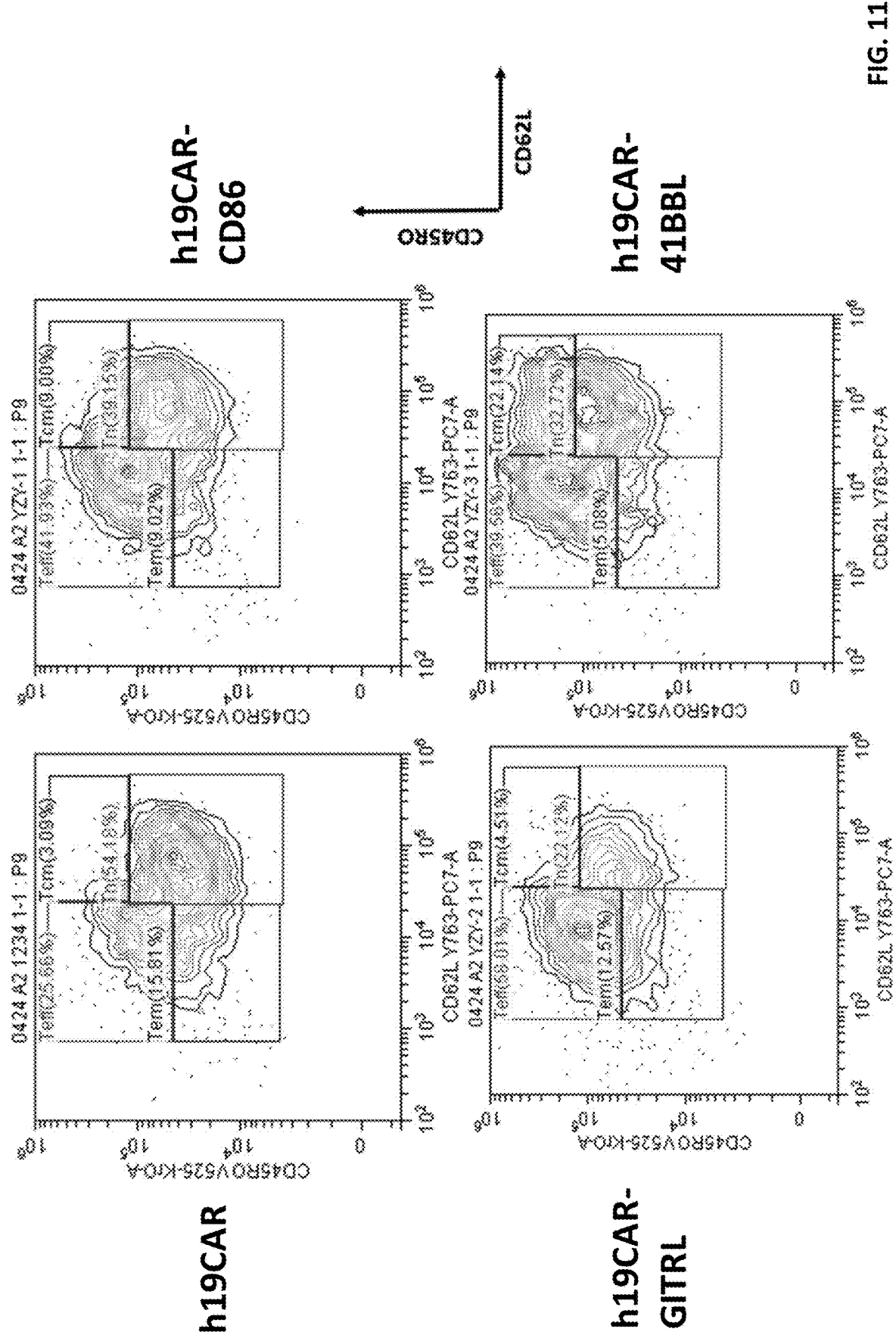
FIG. 11 is the results of memory maker expression in various CAR T cells.
Figure 12:
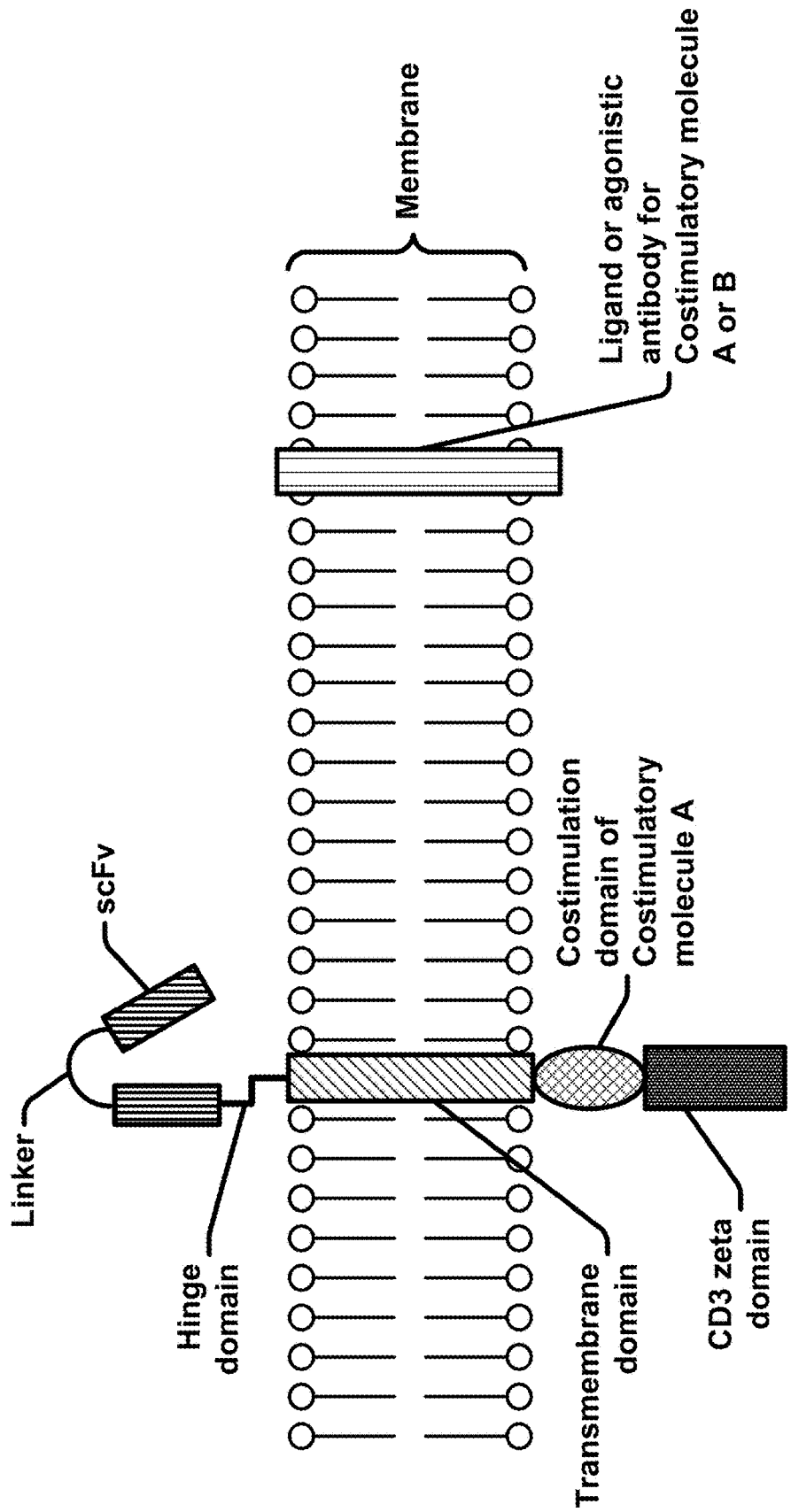
FIG. 12 is a schematic diagram illustrating an example of a CAR and a ligand or agonistic antibody for a costimulatory molecule.
Figure 13:
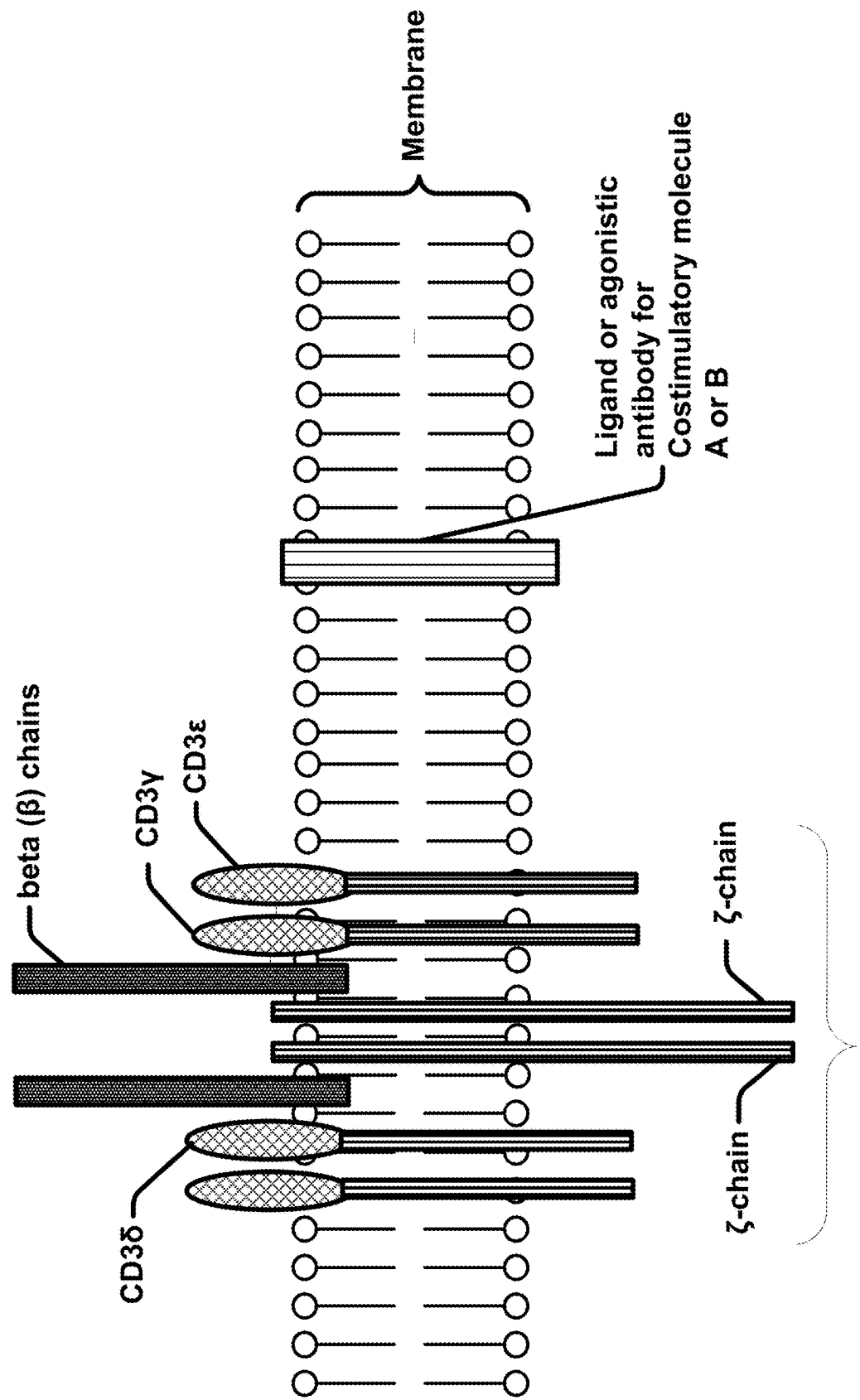
FIG. 13 is a schematic diagram illustrating an example of a TCR and a ligand or agonistic antibody for a costimulatory molecule.

FIG. 11 shows the results of memory maker expression in various CAR T cells. Cells were cultured to day 8, and then hCD19CAR, hCD19CAR-CD86, hCD19CAR-GITRL, hCD19CAR-41BBL, and hCD19CAR-CD80 CAR ratios were leveled using NT cells. $3\times10^4$ CAR+ cells were co-cultured with $10^4$ Nalm-6 cells and $9\times10^4$ Nalm-6 cells, respectively. The expression of CD45RO and CD62L were measured in CAR T cells in 24 hours after the co-culturing. The figure shows the expression levels of CD45RO and CD62L in hCD19CAR, hCD19CAR-CD86, hCD19CAR-GITRL, hCD19CAR-41BBL, hCD19CAR-CD80 cells co-cultured with nalm6 cells, respectively. It can be seen that the Tn expression of h19CAR-GITRL was significantly higher than other groups, indicating that the degree of activation is significantly higher than in other groups and demonstrating that GITRL helped CART cells with their activation the killing process. It can be activated rapidly, and CART cells rapidly differentiate into the killing function of Teff cell form effector cells.

TABLE 3

| Identifier | SEQ ID NO: | Identifier | SEQ ID NO: |
|---|---|---|---|
| SP | 1 | scFv CD207 | 16 |
| αCD19-scFv | 2 | Prolactin (ligand) | 17 |
| CD8 hinge & TM | 3 | scFv CD3 | 18 |
| CD3 zeta | 4 | scFv CD4 | 18 |
| 41BB cytoplasmic domain | 5 | scFv CD4 | 19 |
| 41BB ligand | 6 | scFv CD5 | 20 |
| GITR cytoplasmic domain | 7 | hCD19CAR-CD80 | 21 |
| GITR ligand | 8 | hCD19CAR-CD86 | 22 |
| CD8 hinge & ICOS TM & ICOS cytoplasmic domain | 9 | hCD19CAR-GITRL | 23 |
| ICOS Ligand | 10 | hCD19CAR-41BBL | 24 |
| scFv FZD10 | 11 | hCD19CAR-ICOSL | 25 |
| scFv TSHR | 12 | CAR-CD80 | 26 |
| scFv PRLR | 13 | CAR-CD86 | 27 |
| scFv Muc 17 | 14 | CAR-GITRL | 28 |
| scFv GUCY2C | 15 | CAR-41BBL | 29 |
| GS linker | 31 | CAR-ICOSL | 30 |

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A modified cell comprising a first nucleic acid encoding a chimeric antigen receptor (CAR) and a second nucleic acid encoding an agent binding a first co-stimulatory molecule,
wherein the CAR comprises an extracellular domain, a transmembrane domain, and an intracellular domain, the extracellular domain binds an antigen, and the intracellular domain comprises an intracellular domain of a first co-stimulatory molecule and a second co-stimulatory molecule,
wherein the first co-stimulatory molecule is GITR, and the second co-stimulatory molecule is 4-1BB, and the agent binding the first co-stimulatory molecule is glucocorticoid-induced TNFR-related protein ligand (GITRL), and
wherein the modified cell comprises a nucleic acid encoding the amino acid sequences SEQ ID NOs: 1, 2, 3, 5, 4, and 8 in 5' to 3' order.

2. The modified cell of claim 1, wherein the agent is located on the surface of the cell.

3. The modified cell of claim 1, wherein the CAR further comprises an antigen binding domain that binds a tumor antigen, and a CD3 zeta signaling domain.

4. The modified cell of claim 3, wherein the tumor antigen is HER2, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8.

5. The modified cell of claim 1, wherein the modified cell is a T cell, NK cell, or dendritic cell.

6. A composition comprising a population of the modified cells of claim 4.

7. A method of enhancing T cell response in a subject or treating a tumor of the subject, the method comprising: administering an effective amount of the composition of claim 6.

8. A polynucleotide comprising the nucleic acids encoding the CAR and the agent in the modified cell of claim 1.

9. The modified cell of claim 1, wherein the second nucleic acid is an exogenous molecule that is introduced into the modified cell.

* * * * *

SEQUENCE LISTING

<160> NUMBER OF SEQ ID NOS: 32

<210> SEQ ID NO 1
<211> LENGTH: 21
<212> TYPE: PRT
<213> ORGANISM: Artificial Sequence
<220> FEATURE:
<223> OTHER INFORMATION: Synthesized

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 242
<212> TYPE: PRT

```
<213> ORGANISM: Artificial Sequence
<220> FEATURE:
<223> OTHER INFORMATION: Synthesized

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
            130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
            165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
            210                 215                 220

Gly Ser Tyr Ala Met Asp Tyr Trp Gly Gln Gly Thr Ser Val Thr Val
225                 230                 235                 240

Ser Ser

<210> SEQ ID NO 3
<211> LENGTH: 69
<212> TYPE: PRT
<213> ORGANISM: Artificial Sequence
<220> FEATURE:
<223> OTHER INFORMATION: Synthesized

<400> SEQUENCE: 3

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
            50                  55                  60

Ile Thr Leu Tyr Cys
65
```

```
<210> SEQ ID NO 4
<211> LENGTH: 112
<212> TYPE: PRT
<213> ORGANISM: Homo sapiens

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 42
<212> TYPE: PRT
<213> ORGANISM: Homo sapiens

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 6
<211> LENGTH: 254
<212> TYPE: PRT
<213> ORGANISM: Homo sapiens

<400> SEQUENCE: 6

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140
```

```
Phe Gln Leu Glu Leu Arg Arg Val Val Ala Gly Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 7
<211> LENGTH: 58
<212> TYPE: PRT
<213> ORGANISM: Homo sapiens

<400> SEQUENCE: 7

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
                20                  25                  30

Arg Ser Cys Gln Phe Pro Glu Glu Arg Gly Glu Arg Ser Ala Glu
            35                  40                  45

Glu Lys Gly Arg Leu Gly Asp Leu Trp Val
    50                  55

<210> SEQ ID NO 8
<211> LENGTH: 199
<212> TYPE: PRT
<213> ORGANISM: Homo sapiens

<400> SEQUENCE: 8

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
                20                  25                  30

Leu Ser His Ser Arg Thr Gln Gly Ala Gln Arg Ser Ser Trp Lys Leu
            35                  40                  45

Trp Leu Phe Cys Ser Ile Val Met Leu Leu Phe Leu Cys Ser Phe Ser
        50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160
```

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

<210> SEQ ID NO 9
<211> LENGTH: 104
<212> TYPE: PRT
<213> ORGANISM: Homo sapiens

<400> SEQUENCE: 9

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Leu
        35                  40                  45

Pro Ile Gly Cys Ala Ala Phe Val Val Cys Ile Leu Gly Cys Ile
    50                  55                  60

Leu Ile Cys Trp Leu Thr Lys Lys Lys Tyr Ser Ser Val His Asp
65                  70                  75                  80

Pro Asn Gly Glu Tyr Met Phe Met Arg Ala Val Asn Thr Ala Lys Lys
                85                  90                  95

Ser Arg Leu Thr Asp Val Thr Leu
            100

<210> SEQ ID NO 10
<211> LENGTH: 302
<212> TYPE: PRT
<213> ORGANISM: Homo sapiens

<400> SEQUENCE: 10

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

```
Asn Ser Leu Leu Asp Gln Ala Leu Gln Asn Asp Thr Val Phe Leu Asn
            180                 185                 190

Met Arg Gly Leu Tyr Asp Val Ser Val Leu Arg Ile Ala Arg Thr
            195                 200                 205

Pro Ser Val Asn Ile Gly Cys Cys Ile Glu Asn Val Leu Leu Gln Gln
            210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Val Val Ala Val Ala
            260                 265                 270

Ile Gly Trp Val Cys Arg Asp Arg Cys Leu Gln His Ser Tyr Ala Gly
            275                 280                 285

Ala Trp Ala Val Ser Pro Glu Thr Glu Leu Thr Gly His Val
            290                 295                 300

<210> SEQ ID NO 11
<211> LENGTH: 237
<212> TYPE: PRT
<213> ORGANISM: Artificial Sequence
<220> FEATURE:
<223> OTHER INFORMATION: Synthesized

<400> SEQUENCE: 11

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Gly Ser Gly Gly Gly
            100                 105                 110

Gly Ser Gly Gly Gly Gly Ser Glu Val Gln Leu Gln Gln Ser Gly Ala
            115                 120                 125

Glu Leu Val Lys Pro Gly Ala Ser Val Lys Leu Ser Cys Thr Ala Ser
            130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
            195                 200                 205

Asp Thr Ala Val Tyr Tyr Cys Ala Arg Gly Ala Arg Gly Ser Arg Phe
            210                 215                 220

Ala Tyr Trp Gly Gln Gly Thr Leu Val Thr Val Ser Ala
225                 230                 235
```

```
<210> SEQ ID NO 12
<211> LENGTH: 244
<212> TYPE: PRT
<213> ORGANISM: Artificial Sequence
<220> FEATURE:
<223> OTHER INFORMATION: Synthesized

<400> SEQUENCE: 12

Gln Ser Val Leu Thr Gln Pro Pro Ser Val Ser Ala Ala Pro Gly Gln
1               5                   10                  15

Lys Val Thr Ile Ser Cys Ser Gly Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Ser Gly Gly Gly Ser Glu Val Gln
            115                 120                 125

Leu Val Gln Ser Gly Ala Glu Val Lys Lys Pro Gly Gln Ser Leu Lys
    130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
    210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 13
<211> LENGTH: 252
<212> TYPE: PRT
<213> ORGANISM: Artificial Sequence
<220> FEATURE:
<223> OTHER INFORMATION: Synthesized

<400> SEQUENCE: 13

Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
50                  55                  60
```

```
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Gly
                 85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
        115                 120                 125

Glu Val Gln Leu Val Glu Ser Gly Gly Asp Leu Val Lys Pro Gly Gly
130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
            180                 185                 190

Lys Gly Arg Phe Thr Ile Ser Arg Asp Asn Ala Lys Asn Thr Leu Tyr
        195                 200                 205

Leu Gln Met Ser Ser Leu Lys Ser Glu Asp Ser Ala Met Tyr Tyr Cys
210                 215                 220

Ala Arg His Arg Gly Asn Tyr Tyr Ala Thr Tyr Tyr Tyr Ala Met Asp
225                 230                 235                 240

Tyr Trp Gly Gln Gly Thr Ser Val Thr Val Ser Ser
                245                 250

<210> SEQ ID NO 14
<211> LENGTH: 243
<212> TYPE: PRT
<213> ORGANISM: Artificial Sequence
<220> FEATURE:
<223> OTHER INFORMATION: Synthesized

<400> SEQUENCE: 14

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His His Glu Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Gln
        115                 120                 125

Pro Gly Ala Glu Leu Val Arg Pro Gly Ala Ser Val Lys Leu Ser Cys
    130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175
```

Asp Ser Glu Thr His Tyr Asn Gln Lys Phe Lys Asp Lys Ala Ile Leu
            180                 185                 190

Thr Val Asp Lys Ser Ser Thr Ala Tyr Met Gln Leu Ser Ser Leu
        195                 200                 205

Thr Ser Glu Asp Ser Ala Val Tyr Tyr Cys Ala Arg Gly Pro Tyr Tyr
    210                 215                 220

Gly Thr Asn Pro Trp Phe Pro Tyr Trp Gly Gln Gly Thr Leu Val Thr
225                 230                 235                 240

Val Ser Ser

<210> SEQ ID NO 15
<211> LENGTH: 241
<212> TYPE: PRT
<213> ORGANISM: Artificial Sequence
<220> FEATURE:
<223> OTHER INFORMATION: Synthesized

<400> SEQUENCE: 15

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
    130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Phe Asp His Trp Gly Gln Gly Thr Leu Val Thr Val Ser
225                 230                 235                 240

Ser

<210> SEQ ID NO 16
<211> LENGTH: 246
<212> TYPE: PRT
<213> ORGANISM: Artificial Sequence
<220> FEATURE:
<223> OTHER INFORMATION: Synthesized

<400> SEQUENCE: 16

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Ser Gly Gly Gly Gly
        115                 120                 125

Ser Gln Val Gln Leu Arg Gln Ser Gly Pro Glu Leu Val Lys Pro Gly
130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
                245

<210> SEQ ID NO 17
<211> LENGTH: 199
<212> TYPE: PRT
<213> ORGANISM: Homo sapiens

<400> SEQUENCE: 17

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
                85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
            115                 120                 125

Gly Met Glu Leu Ile Val Ser Gln Val His Pro Glu Thr Lys Glu Asn
        130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Lys Cys Arg
            180                 185                 190

Ile Ile His Asn Asn Asn Cys
        195

<210> SEQ ID NO 18
<211> LENGTH: 240
<212> TYPE: PRT
<213> ORGANISM: Artificial Sequence
<220> FEATURE:
<223> OTHER INFORMATION: Synthesized

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Gly Gly Gly Gly Gly Ser Gly Gly Gly Ser Gly Gly Gly Gly Ser
        115                 120                 125

Asp Ile Val Met Thr Gln Ser Pro Asp Ser Leu Ala Val Ser Leu Gly
        130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
            180                 185                 190

Pro Asp Arg Phe Ser Gly Ser Gly Ser Gly Thr Asp Phe Thr Leu Thr
        195                 200                 205

Ile Ser Ser Leu Gln Ala Glu Asp Val Ala Val Tyr Tyr Cys Thr Gln
    210                 215                 220

Ser Phe Ile Leu Arg Thr Phe Gly Gln Gly Thr Lys Val Glu Ile Lys
225                 230                 235                 240

<210> SEQ ID NO 19
<211> LENGTH: 285
<212> TYPE: PRT
<213> ORGANISM: Artificial Sequence
<220> FEATURE:
<223> OTHER INFORMATION: Synthesized

<400> SEQUENCE: 19

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys Gly Gly Gly Gly Ser Gly Gly Gly Gly Ser Gly Gly Gly Gly
    130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
    210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285

<210> SEQ ID NO 20
<211> LENGTH: 242
<212> TYPE: PRT
<213> ORGANISM: Artificial Sequence
<220> FEATURE:
<223> OTHER INFORMATION: Synthesized

<400> SEQUENCE: 20

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly

```
                 50                  55                  60
Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                 85                  90                  95

Phe Gly Ser Gly Thr Lys Leu Glu Ile Lys Gly Gly Gly Gly Ser
                100                 105                 110

Gly Gly Gly Gly Ser Gly Gly Gly Ser Gln Val Thr Leu Lys Glu
                115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Val Tyr Tyr Asn Pro Ser Leu Lys Ser Arg Leu Thr
                180                 185                 190

Ile Thr Lys Asp Ala Ser Lys Asp Gln Val Ser Leu Lys Leu Ser Ser
                195                 200                 205

Val Thr Ala Ala Asp Thr Ala Val Tyr Tyr Cys Val Arg Arg Arg Ala
210                 215                 220

Thr Gly Thr Gly Phe Asp Tyr Trp Gly Gln Gly Thr Leu Val Thr Val
225                 230                 235                 240

Ser Ser

<210> SEQ ID NO 21
<211> LENGTH: 796
<212> TYPE: PRT
<213> ORGANISM: Artificial Sequence
<220> FEATURE:
<223> OTHER INFORMATION: Synthesized

<400> SEQUENCE: 21

Met Ala Leu Pro Val Thr Ala Leu Leu Leu Pro Leu Ala Leu Leu Leu
 1               5                  10                  15

His Ala Ala Arg Pro Asp Ile Gln Met Thr Gln Ser Pro Ser Ser Leu
                 20                  25                  30

Ser Ala Ser Val Gly Asp Arg Val Thr Ile Thr Cys Arg Ala Ser Gln
             35                  40                  45

Asp Ile Ser Lys Tyr Leu Asn Trp Tyr Gln Gln Lys Pro Gly Lys Ala
         50                  55                  60

Pro Lys Leu Leu Ile Tyr His Thr Ser Arg Leu His Ser Gly Val Pro
 65                  70                  75                  80

Ser Arg Phe Ser Gly Ser Gly Ser Gly Thr Asp Phe Thr Leu Thr Ile
                 85                  90                  95

Ser Ser Leu Gln Pro Glu Asp Phe Ala Thr Tyr Tyr Cys Gln Gln Gly
                100                 105                 110

Asn Thr Leu Pro Tyr Thr Phe Gly Gln Gly Thr Lys Val Glu Ile Lys
             115                 120                 125

Gly Gly Gly Gly Ser Gly Gly Gly Ser Gly Gly Gly Ser Glu
130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Val Ser Leu Pro Asp Tyr Gly
                165                 170                 175
```

```
Val Ser Trp Val Arg Gln Ala Pro Gly Lys Gly Leu Glu Trp Val Ser
                180                 185                 190

Val Ile Trp Gly Ser Glu Thr Thr Tyr Tyr Asn Ser Ala Leu Lys Ser
                195                 200                 205

Arg Phe Thr Ile Ser Arg Asp Asn Ala Lys Asn Ser Leu Tyr Leu Gln
                210                 215                 220

Met Asn Ser Leu Arg Ala Glu Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                    245                 250                 255

Thr Leu Val Thr Val Ser Ser Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                    325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
                370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                    405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Gly Ala Thr Asn Phe Ser Leu Leu
                    485                 490                 495

Lys Gln Ala Gly Asp Val Glu Glu Asn Pro Gly Pro Met Gly His Thr
                500                 505                 510

Arg Arg Gln Gly Thr Ser Pro Ser Lys Cys Pro Tyr Leu Asn Phe Phe
                515                 520                 525

Gln Leu Leu Val Leu Ala Gly Leu Ser His Phe Cys Ser Gly Val Ile
530                 535                 540

His Val Thr Lys Glu Val Lys Glu Val Ala Thr Leu Ser Cys Gly His
                    545                 550                 555                 560

Asn Val Ser Val Glu Glu Leu Ala Gln Thr Arg Ile Tyr Trp Gln Lys
                565                 570                 575

Glu Lys Lys Met Val Leu Thr Met Met Ser Gly Asp Met Asn Ile Trp
                580                 585                 590
```

```
Pro Glu Tyr Lys Asn Arg Thr Ile Phe Asp Ile Thr Asn Asn Leu Ser
            595                 600                 605

Ile Val Ile Leu Ala Leu Arg Pro Ser Asp Glu Gly Thr Tyr Glu Cys
610                 615                 620

Val Val Leu Lys Tyr Glu Lys Asp Ala Phe Lys Arg Glu His Leu Ala
625                 630                 635                 640

Glu Val Thr Leu Ser Val Lys Ala Asp Phe Pro Thr Pro Ser Ile Ser
            645                 650                 655

Asp Phe Glu Ile Pro Thr Ser Asn Ile Arg Arg Ile Ile Cys Ser Thr
            660                 665                 670

Ser Gly Gly Phe Pro Glu Pro His Leu Ser Trp Leu Glu Asn Gly Glu
            675                 680                 685

Glu Leu Asn Ala Ile Asn Thr Thr Val Ser Gln Asp Pro Glu Thr Glu
            690                 695                 700

Leu Tyr Ala Val Ser Ser Lys Leu Asp Phe Asn Met Thr Thr Asn His
705                 710                 715                 720

Ser Phe Met Cys Leu Ile Lys Tyr Gly His Leu Arg Val Asn Gln Thr
            725                 730                 735

Phe Asn Trp Asn Thr Thr Lys Gln Glu His Phe Pro Asp Asn Leu Leu
            740                 745                 750

Pro Ser Trp Ala Ile Thr Leu Ile Ser Val Asn Gly Ile Phe Val Ile
            755                 760                 765

Cys Cys Leu Thr Tyr Cys Phe Ala Pro Arg Cys Arg Glu Arg Arg Arg
            770                 775                 780

Asn Glu Arg Leu Arg Arg Glu Ser Val Arg Pro Val
785                 790                 795

<210> SEQ ID NO 22
<211> LENGTH: 837
<212> TYPE: PRT
<213> ORGANISM: Artificial Sequence
<220> FEATURE:
<223> OTHER INFORMATION: Synthesized

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Lys Ala
    50                  55                  60

Pro Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Gly
            100                 105                 110

Asn Thr Leu Pro Tyr Thr Phe Gly Gln Gly Thr Lys Val Glu Ile Lys
        115                 120                 125

Gly Gly Gly Gly Ser Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160
```

```
Leu Arg Leu Ser Cys Ala Ala Ser Gly Val Ser Leu Pro Asp Tyr Gly
            165                 170                 175

Val Ser Trp Val Arg Gln Ala Pro Gly Lys Gly Leu Glu Trp Val Ser
        180                 185                 190

Val Ile Trp Gly Ser Glu Thr Thr Tyr Tyr Asn Ser Ala Leu Lys Ser
    195                 200                 205

Arg Phe Thr Ile Ser Arg Asp Asn Ala Lys Asn Ser Leu Tyr Leu Gln
    210                 215                 220

Met Asn Ser Leu Arg Ala Glu Asp Thr Ala Val Tyr Tyr Cys Ala Lys
225                 230                 235                 240

His Tyr Tyr Gly Gly Ser Tyr Ala Met Asp Tyr Trp Gly Gln Gly
            245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Gly Ala Thr Asn Phe Ser Leu Leu
            485                 490                 495

Lys Gln Ala Gly Asp Val Glu Glu Asn Pro Gly Pro Met Asp Pro Gln
            500                 505                 510

Cys Thr Met Gly Leu Ser Asn Ile Leu Phe Val Met Ala Phe Leu Leu
        515                 520                 525

Ser Gly Ala Ala Pro Leu Lys Ile Gln Ala Tyr Phe Asn Glu Thr Ala
    530                 535                 540

Asp Leu Pro Cys Gln Phe Ala Asn Ser Gln Asn Gln Ser Leu Ser Glu
545                 550                 555                 560

Leu Val Val Phe Trp Gln Asp Gln Glu Asn Leu Val Leu Asn Glu Val
            565                 570                 575

Tyr Leu Gly Lys Glu Lys Phe Asp Ser Val His Ser Lys Tyr Met Gly
```

```
                580             585             590
Arg Thr Ser Phe Asp Ser Asp Ser Trp Thr Leu Arg Leu His Asn Leu
        595             600             605
Gln Ile Lys Asp Lys Gly Leu Tyr Gln Cys Ile Ile His His Lys Lys
        610             615             620
Pro Thr Gly Met Ile Arg Ile His Gln Met Asn Ser Glu Leu Ser Val
625             630             635             640
Leu Ala Asn Phe Ser Gln Pro Glu Ile Val Pro Ile Ser Asn Ile Thr
            645             650             655
Glu Asn Val Tyr Ile Asn Leu Thr Cys Ser Ser Ile His Gly Tyr Pro
            660             665             670
Glu Pro Lys Lys Met Ser Val Leu Leu Arg Thr Lys Asn Ser Thr Ile
        675             680             685
Glu Tyr Asp Gly Val Met Gln Lys Ser Gln Asp Asn Val Thr Glu Leu
        690             695             700
Tyr Asp Val Ser Ile Ser Leu Ser Val Ser Phe Pro Asp Val Thr Ser
705             710             715             720
Asn Met Thr Ile Phe Cys Ile Leu Glu Thr Asp Lys Thr Arg Leu Leu
            725             730             735
Ser Ser Pro Phe Ser Ile Glu Leu Glu Asp Pro Gln Pro Pro Pro Asp
            740             745             750
His Ile Pro Trp Ile Thr Ala Val Leu Pro Thr Val Ile Ile Cys Val
        755             760             765
Met Val Phe Cys Leu Ile Leu Trp Lys Trp Lys Lys Lys Lys Arg Pro
770             775             780
Arg Asn Ser Tyr Lys Cys Gly Thr Asn Thr Met Glu Arg Glu Glu Ser
785             790             795             800
Glu Gln Thr Lys Lys Arg Glu Lys Ile His Ile Pro Glu Arg Ser Asp
                805             810             815
Glu Ala Gln Arg Val Phe Lys Ser Ser Lys Thr Ser Ser Cys Asp Lys
            820             825             830
Ser Asp Thr Cys Phe
        835

<210> SEQ ID NO 23
<211> LENGTH: 707
<212> TYPE: PRT
<213> ORGANISM: Artificial Sequence
<220> FEATURE:
<223> OTHER INFORMATION: Synthesized

<400> SEQUENCE: 23

Met Ala Leu Pro Val Thr Ala Leu Leu Leu Pro Leu Ala Leu Leu Leu
1               5                   10                  15
His Ala Ala Arg Pro Asp Ile Gln Met Thr Gln Ser Pro Ser Ser Leu
            20                  25                  30
Ser Ala Ser Val Gly Asp Arg Val Thr Ile Thr Cys Arg Ala Ser Gln
        35                  40                  45
Asp Ile Ser Lys Tyr Leu Asn Trp Tyr Gln Gln Lys Pro Gly Lys Ala
    50                  55                  60
Pro Lys Leu Leu Ile Tyr His Thr Ser Arg Leu His Ser Gly Val Pro
65                  70                  75                  80
Ser Arg Phe Ser Gly Ser Gly Ser Gly Thr Asp Phe Thr Leu Thr Ile
                85                  90                  95
Ser Ser Leu Gln Pro Glu Asp Phe Ala Thr Tyr Tyr Cys Gln Gln Gly
```

```
            100                 105                 110
Asn Thr Leu Pro Tyr Thr Phe Gly Gln Gly Thr Lys Val Glu Ile Lys
            115                 120                 125
Gly Gly Gly Gly Ser Gly Gly Gly Gly Ser Gly Gly Gly Gly Ser Glu
            130                 135                 140
Val Gln Leu Val Glu Ser Gly Gly Gly Leu Val Gln Pro Gly Gly Ser
145                 150                 155                 160
Leu Arg Leu Ser Cys Ala Ala Ser Gly Val Ser Leu Pro Asp Tyr Gly
                    165                 170                 175
Val Ser Trp Val Arg Gln Ala Pro Gly Lys Gly Leu Glu Trp Val Ser
                    180                 185                 190
Val Ile Trp Gly Ser Glu Thr Thr Tyr Tyr Asn Ser Ala Leu Lys Ser
                    195                 200                 205
Arg Phe Thr Ile Ser Arg Asp Asn Ala Lys Asn Ser Leu Tyr Leu Gln
            210                 215                 220
Met Asn Ser Leu Arg Ala Glu Asp Thr Ala Val Tyr Tyr Cys Ala Lys
225                 230                 235                 240
His Tyr Tyr Tyr Gly Gly Ser Tyr Ala Met Asp Tyr Trp Gly Gln Gly
                    245                 250                 255
Thr Leu Val Thr Val Ser Ser Thr Thr Thr Pro Ala Pro Arg Pro Pro
            260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
            290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                    325                 330                 335
Lys Lys Leu Leu Tyr Ile Phe Lys Gln Pro Phe Met Arg Pro Val Gln
                    340                 345                 350
Thr Thr Gln Glu Glu Asp Gly Cys Ser Cys Arg Phe Pro Glu Glu Glu
            355                 360                 365
Glu Gly Gly Cys Glu Leu Arg Val Lys Phe Ser Arg Ser Ala Asp Ala
            370                 375                 380
Pro Ala Tyr Gln Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                    405                 410                 415
Pro Glu Met Gly Gly Lys Pro Arg Arg Lys Asn Pro Gln Glu Gly Leu
                    420                 425                 430
Tyr Asn Glu Leu Gln Lys Asp Lys Met Ala Glu Ala Tyr Ser Glu Ile
            435                 440                 445
Gly Met Lys Gly Glu Arg Arg Arg Gly Lys Gly His Asp Gly Leu Tyr
            450                 455                 460
Gln Gly Leu Ser Thr Ala Thr Lys Asp Thr Tyr Asp Ala Leu His Met
465                 470                 475                 480
Gln Ala Leu Pro Pro Arg Gly Ser Gly Ala Thr Asn Phe Ser Leu Leu
                    485                 490                 495
Lys Gln Ala Gly Asp Val Glu Glu Asn Pro Gly Pro Met Thr Leu His
                    500                 505                 510
Pro Ser Pro Ile Thr Cys Glu Phe Leu Phe Ser Thr Ala Leu Ile Ser
            515                 520                 525
```

```
Pro Lys Met Cys Leu Ser His Leu Glu Asn Met Pro Leu Ser His Ser
    530                 535                 540
Arg Thr Gln Gly Ala Gln Arg Ser Ser Trp Lys Leu Trp Leu Phe Cys
545                 550                 555                 560
Ser Ile Val Met Leu Leu Phe Leu Cys Ser Phe Ser Trp Leu Ile Phe
                565                 570                 575
Ile Phe Leu Gln Leu Glu Thr Ala Lys Glu Pro Cys Met Ala Lys Phe
            580                 585                 590
Gly Pro Leu Pro Ser Lys Trp Gln Met Ala Ser Ser Glu Pro Pro Cys
        595                 600                 605
Val Asn Lys Val Ser Asp Trp Lys Leu Glu Ile Leu Gln Asn Gly Leu
610                 615                 620
Tyr Leu Ile Tyr Gly Gln Val Ala Pro Asn Ala Asn Tyr Asn Asp Val
625                 630                 635                 640
Ala Pro Phe Glu Val Arg Leu Tyr Lys Asn Lys Asp Met Ile Gln Thr
                645                 650                 655
Leu Thr Asn Lys Ser Lys Ile Gln Asn Val Gly Gly Thr Tyr Glu Leu
            660                 665                 670
His Val Gly Asp Thr Ile Asp Leu Ile Phe Asn Ser Glu His Gln Val
        675                 680                 685
Leu Lys Asn Asn Thr Tyr Trp Gly Ile Ile Leu Leu Ala Asn Pro Gln
690                 695                 700
Phe Ile Ser
705

<210> SEQ ID NO 24
<211> LENGTH: 762
<212> TYPE: PRT
<213> ORGANISM: Artificial Sequence
<220> FEATURE:
<223> OTHER INFORMATION: Synthesized

<400> SEQUENCE: 24

Met Ala Leu Pro Val Thr Ala Leu Leu Leu Pro Leu Ala Leu Leu Leu
1               5                   10                  15
His Ala Ala Arg Pro Asp Ile Gln Met Thr Gln Ser Pro Ser Ser Leu
            20                  25                  30
Ser Ala Ser Val Gly Asp Arg Val Thr Ile Thr Cys Arg Ala Ser Gln
        35                  40                  45
Asp Ile Ser Lys Tyr Leu Asn Trp Tyr Gln Gln Lys Pro Gly Lys Ala
    50                  55                  60
Pro Lys Leu Leu Ile Tyr His Thr Ser Arg Leu His Ser Gly Val Pro
65                  70                  75                  80
Ser Arg Phe Ser Gly Ser Gly Ser Gly Thr Asp Phe Thr Leu Thr Ile
                85                  90                  95
Ser Ser Leu Gln Pro Glu Asp Phe Ala Thr Tyr Tyr Cys Gln Gln Gly
            100                 105                 110
Asn Thr Leu Pro Tyr Thr Phe Gly Gln Gly Thr Lys Val Glu Ile Lys
        115                 120                 125
Gly Gly Gly Gly Ser Gly Gly Gly Ser Gly Gly Gly Gly Ser Glu
        130                 135                 140
Val Gln Leu Val Glu Ser Gly Gly Gly Leu Val Gln Pro Gly Gly Ser
145                 150                 155                 160
Leu Arg Leu Ser Cys Ala Ala Ser Gly Val Ser Leu Pro Asp Tyr Gly
                165                 170                 175
```

```
Val Ser Trp Val Arg Gln Ala Pro Gly Lys Gly Leu Glu Trp Val Ser
            180                 185                 190
Val Ile Trp Gly Ser Glu Thr Thr Tyr Tyr Asn Ser Ala Leu Lys Ser
        195                 200                 205
Arg Phe Thr Ile Ser Arg Asp Asn Ala Lys Asn Ser Leu Tyr Leu Gln
    210                 215                 220
Met Asn Ser Leu Arg Ala Glu Asp Thr Ala Val Tyr Tyr Cys Ala Lys
225                 230                 235                 240
His Tyr Tyr Tyr Gly Ser Tyr Ala Met Asp Tyr Trp Gly Gln Gly
                245                 250                 255
Thr Leu Val Thr Val Ser Ser Thr Thr Pro Ala Pro Arg Pro Pro
            260                 265                 270
Thr Pro Ala Pro Thr Ile Ala Ser Gln Pro Leu Ser Leu Arg Pro Glu
        275                 280                 285
Ala Cys Arg Pro Ala Ala Gly Gly Ala Val His Thr Arg Gly Leu Asp
    290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                325                 330                 335
Lys Lys Leu Leu Tyr Ile Phe Lys Gln Pro Phe Met Arg Pro Val Gln
            340                 345                 350
Thr Thr Gln Glu Glu Asp Gly Cys Ser Cys Arg Phe Pro Glu Glu Glu
        355                 360                 365
Glu Gly Gly Cys Glu Leu Arg Val Lys Phe Ser Arg Ser Ala Asp Ala
    370                 375                 380
Pro Ala Tyr Gln Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                405                 410                 415
Pro Glu Met Gly Gly Lys Pro Arg Arg Lys Asn Pro Gln Glu Gly Leu
            420                 425                 430
Tyr Asn Glu Leu Gln Lys Asp Lys Met Ala Glu Ala Tyr Ser Glu Ile
        435                 440                 445
Gly Met Lys Gly Glu Arg Arg Arg Gly Lys Gly His Asp Gly Leu Tyr
    450                 455                 460
Gln Gly Leu Ser Thr Ala Thr Lys Asp Thr Tyr Asp Ala Leu His Met
465                 470                 475                 480
Gln Ala Leu Pro Pro Arg Gly Ser Gly Ala Thr Asn Phe Ser Leu Leu
                485                 490                 495
Lys Gln Ala Gly Asp Val Glu Glu Asn Pro Gly Pro Met Glu Tyr Ala
            500                 505                 510
Ser Asp Ala Ser Leu Asp Pro Glu Ala Pro Trp Pro Pro Ala Pro Arg
        515                 520                 525
Ala Arg Ala Cys Arg Val Leu Pro Trp Ala Leu Val Ala Gly Leu Leu
    530                 535                 540
Leu Leu Leu Leu Leu Ala Ala Ala Cys Ala Val Phe Leu Ala Cys Pro
545                 550                 555                 560
Trp Ala Val Ser Gly Ala Arg Ala Ser Pro Gly Ser Ala Ala Ser Pro
                565                 570                 575
Arg Leu Arg Glu Gly Pro Glu Leu Ser Pro Asp Asp Pro Ala Gly Leu
            580                 585                 590
```

```
Leu Asp Leu Arg Gln Gly Met Phe Ala Gln Leu Val Ala Gln Asn Val
            595                 600                 605

Leu Leu Ile Asp Gly Pro Leu Ser Trp Tyr Ser Asp Pro Gly Leu Ala
    610                 615                 620

Gly Val Ser Leu Thr Gly Gly Leu Ser Tyr Lys Glu Asp Thr Lys Glu
625                 630                 635                 640

Leu Val Val Ala Lys Ala Gly Val Tyr Tyr Val Phe Phe Gln Leu Glu
                645                 650                 655

Leu Arg Arg Val Val Ala Gly Glu Ser Gly Ser Val Ser Leu Ala
            660                 665                 670

Leu His Leu Gln Pro Leu Arg Ser Ala Gly Ala Ala Leu Ala
    675                 680                 685

Leu Thr Val Asp Leu Pro Pro Ala Ser Ser Glu Ala Arg Asn Ser Ala
    690                 695                 700

Phe Gly Phe Gln Gly Arg Leu Leu His Leu Ser Ala Gly Gln Arg Leu
705                 710                 715                 720

Gly Val His Leu His Thr Glu Ala Arg Ala Arg His Ala Trp Gln Leu
                725                 730                 735

Thr Gln Gly Ala Thr Val Leu Gly Leu Phe Arg Val Thr Pro Glu Ile
            740                 745                 750

Pro Ala Gly Leu Pro Ser Pro Arg Ser Glu
            755                 760

<210> SEQ ID NO 25
<211> LENGTH: 810
<212> TYPE: PRT
<213> ORGANISM: Artificial Sequence
<220> FEATURE:
<223> OTHER INFORMATION: Synthesized

<400> SEQUENCE: 25

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Asp Ile Ser Lys Tyr Leu Asn Trp Tyr Gln Gln Lys Pro Gly Lys Ala
    50                  55                  60

Pro Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Gly
            100                 105                 110

Asn Thr Leu Pro Tyr Thr Phe Gly Gln Gly Thr Lys Val Glu Ile Lys
    115                 120                 125

Gly Gly Gly Gly Ser Gly Gly Gly Gly Ser Gly Gly Gly Gly Ser Glu
130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Val Ser Leu Pro Asp Tyr Gly
                165                 170                 175

Val Ser Trp Val Arg Gln Ala Pro Gly Lys Gly Leu Glu Trp Val Ser
            180                 185                 190
```

-continued

```
Val Ile Trp Gly Ser Glu Thr Thr Tyr Tyr Asn Ser Ala Leu Lys Ser
            195                 200                 205

Arg Phe Thr Ile Ser Arg Asp Asn Ala Lys Asn Ser Leu Tyr Leu Gln
        210                 215                 220

Met Asn Ser Leu Arg Ala Glu Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Gly Ala Thr Asn Phe Ser Leu Leu
                485                 490                 495

Lys Gln Ala Gly Asp Val Glu Glu Asn Pro Gly Pro Met Arg Leu Gly
            500                 505                 510

Ser Pro Gly Leu Leu Phe Leu Leu Phe Ser Ser Leu Arg Ala Asp Thr
        515                 520                 525

Gln Glu Lys Glu Val Arg Ala Met Val Gly Ser Asp Val Glu Leu Ser
    530                 535                 540

Cys Ala Cys Pro Glu Gly Ser Arg Phe Asp Leu Asn Asp Val Tyr Val
545                 550                 555                 560

Tyr Trp Gln Thr Ser Glu Ser Lys Thr Val Val Thr Tyr His Ile Pro
                565                 570                 575

Gln Asn Ser Ser Leu Glu Asn Val Asp Ser Arg Tyr Arg Asn Arg Ala
            580                 585                 590

Leu Met Ser Pro Ala Gly Met Leu Arg Gly Asp Phe Ser Leu Arg Leu
        595                 600                 605

Phe Asn Val Thr Pro Gln Asp Glu Gln Lys Phe His Cys Leu Val Leu
```

```
                610                 615                 620
Ser Gln Ser Leu Gly Phe Gln Glu Val Leu Ser Val Glu Val Thr Leu
625                 630                 635                 640

His Val Ala Ala Asn Phe Ser Val Pro Val Ser Ala Pro His Ser
                645                 650                 655

Pro Ser Gln Asp Glu Leu Thr Phe Thr Cys Thr Ser Ile Asn Gly Tyr
                660                 665                 670

Pro Arg Pro Asn Val Tyr Trp Ile Asn Lys Thr Asp Asn Ser Leu Leu
                675                 680                 685

Asp Gln Ala Leu Gln Asn Asp Thr Val Phe Leu Asn Met Arg Gly Leu
                690                 695                 700

Tyr Asp Val Val Ser Val Leu Arg Ile Ala Arg Thr Pro Ser Val Asn
705                 710                 715                 720

Ile Gly Cys Cys Ile Glu Asn Val Leu Leu Gln Gln Asn Leu Thr Val
                725                 730                 735

Gly Ser Gln Thr Gly Asn Asp Ile Gly Glu Arg Asp Lys Ile Thr Glu
                740                 745                 750

Asn Pro Val Ser Thr Gly Glu Lys Asn Ala Ala Thr Trp Ser Ile Leu
                755                 760                 765

Ala Val Leu Cys Leu Leu Val Val Ala Val Ala Ile Gly Trp Val
770                 775                 780

Cys Arg Asp Arg Cys Leu Gln His Ser Tyr Ala Gly Ala Trp Ala Val
785                 790                 795                 800

Ser Pro Glu Thr Glu Leu Thr Gly His Val
                805                 810

<210> SEQ ID NO 26
<211> LENGTH: 533
<212> TYPE: PRT
<213> ORGANISM: Artificial Sequence
<220> FEATURE:
<223> OTHER INFORMATION: Synthesized

<400> SEQUENCE: 26

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
                35                  40                  45

Trp Ala Pro Leu Ala Gly Thr Cys Gly Val Leu Leu Leu Ser Leu Val
                50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Gly Gly Cys Glu Leu Arg
                100                 105                 110

Val Lys Phe Ser Arg Ser Ala Asp Ala Pro Ala Tyr Gln Gln Gly Gln
                115                 120                 125

Asn Gln Leu Tyr Asn Glu Leu Asn Leu Gly Arg Arg Glu Glu Tyr Asp
                130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
```

```
                165                 170                 175
Lys Met Ala Glu Ala Tyr Ser Glu Ile Gly Met Lys Gly Glu Arg Arg
                180                 185                 190

Arg Gly Lys Gly His Asp Gly Leu Tyr Gln Gly Leu Ser Thr Ala Thr
            195                 200                 205

Lys Asp Thr Tyr Asp Ala Leu His Met Gln Ala Leu Pro Pro Arg Gly
        210                 215                 220

Ser Gly Ala Thr Asn Phe Ser Leu Leu Lys Gln Ala Gly Asp Val Glu
225                 230                 235                 240

Glu Asn Pro Gly Pro Met Gly His Thr Arg Arg Gln Gly Thr Ser Pro
                245                 250                 255

Ser Lys Cys Pro Tyr Leu Asn Phe Phe Gln Leu Leu Val Leu Ala Gly
            260                 265                 270

Leu Ser His Phe Cys Ser Gly Val Ile His Val Thr Lys Glu Val Lys
        275                 280                 285

Glu Val Ala Thr Leu Ser Cys Gly His Asn Val Ser Val Glu Glu Leu
    290                 295                 300

Ala Gln Thr Arg Ile Tyr Trp Gln Lys Glu Lys Lys Met Val Leu Thr
305                 310                 315                 320

Met Met Ser Gly Asp Met Asn Ile Trp Pro Glu Tyr Lys Asn Arg Thr
                325                 330                 335

Ile Phe Asp Ile Thr Asn Asn Leu Ser Ile Val Ile Leu Ala Leu Arg
            340                 345                 350

Pro Ser Asp Glu Gly Thr Tyr Glu Cys Val Val Leu Lys Tyr Glu Lys
        355                 360                 365

Asp Ala Phe Lys Arg Glu His Leu Ala Glu Val Thr Leu Ser Val Lys
    370                 375                 380

Ala Asp Phe Pro Thr Pro Ser Ile Ser Asp Phe Glu Ile Pro Thr Ser
385                 390                 395                 400

Asn Ile Arg Arg Ile Ile Cys Ser Thr Ser Gly Gly Phe Pro Glu Pro
                405                 410                 415

His Leu Ser Trp Leu Glu Asn Gly Glu Glu Leu Asn Ala Ile Asn Thr
            420                 425                 430

Thr Val Ser Gln Asp Pro Glu Thr Glu Leu Tyr Ala Val Ser Ser Lys
        435                 440                 445

Leu Asp Phe Asn Met Thr Thr Asn His Ser Phe Met Cys Leu Ile Lys
    450                 455                 460

Tyr Gly His Leu Arg Val Asn Gln Thr Phe Asn Trp Asn Thr Thr Lys
465                 470                 475                 480

Gln Glu His Phe Pro Asp Asn Leu Leu Pro Ser Trp Ala Ile Thr Leu
                485                 490                 495

Ile Ser Val Asn Gly Ile Phe Val Ile Cys Cys Leu Thr Tyr Cys Phe
            500                 505                 510

Ala Pro Arg Cys Arg Glu Arg Arg Arg Asn Glu Arg Leu Arg Arg Glu
        515                 520                 525

Ser Val Arg Pro Val
    530

<210> SEQ ID NO 27
<211> LENGTH: 574
<212> TYPE: PRT
<213> ORGANISM: Artificial Sequence
<220> FEATURE:
<223> OTHER INFORMATION: Synthesized
```

```
<400> SEQUENCE: 27

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
        115                 120                 125

Asn Gln Leu Tyr Asn Glu Leu Asn Leu Gly Arg Arg Glu Glu Tyr Asp
        130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg Gly
210                 215                 220

Ser Gly Ala Thr Asn Phe Ser Leu Leu Lys Gln Ala Gly Asp Val Glu
225                 230                 235                 240

Glu Asn Pro Gly Pro Met Asp Pro Gln Cys Thr Met Gly Leu Ser Asn
                245                 250                 255

Ile Leu Phe Val Met Ala Phe Leu Leu Ser Gly Ala Ala Pro Leu Lys
            260                 265                 270

Ile Gln Ala Tyr Phe Asn Glu Thr Ala Asp Leu Pro Cys Gln Phe Ala
        275                 280                 285

Asn Ser Gln Asn Gln Ser Leu Ser Glu Leu Val Val Phe Trp Gln Asp
        290                 295                 300

Gln Glu Asn Leu Val Leu Asn Glu Val Tyr Leu Gly Lys Glu Lys Phe
305                 310                 315                 320

Asp Ser Val His Ser Lys Tyr Met Gly Arg Thr Ser Phe Asp Ser Asp
                325                 330                 335

Ser Trp Thr Leu Arg Leu His Asn Leu Gln Ile Lys Asp Lys Gly Leu
            340                 345                 350

Tyr Gln Cys Ile Ile His His Lys Lys Pro Thr Gly Met Ile Arg Ile
        355                 360                 365

His Gln Met Asn Ser Glu Leu Ser Val Leu Ala Asn Phe Ser Gln Pro
        370                 375                 380

Glu Ile Val Pro Ile Ser Asn Ile Thr Glu Asn Val Tyr Ile Asn Leu
385                 390                 395                 400

Thr Cys Ser Ser Ile His Gly Tyr Pro Glu Pro Lys Lys Met Ser Val
                405                 410                 415
```

```
Leu Leu Arg Thr Lys Asn Ser Thr Ile Glu Tyr Asp Gly Val Met Gln
                420                 425                 430

Lys Ser Gln Asp Asn Val Thr Glu Leu Tyr Asp Val Ser Ile Ser Leu
            435                 440                 445

Ser Val Ser Phe Pro Asp Val Thr Ser Asn Met Thr Ile Phe Cys Ile
        450                 455                 460

Leu Glu Thr Asp Lys Thr Arg Leu Leu Ser Ser Pro Phe Ser Ile Glu
465                 470                 475                 480

Leu Glu Asp Pro Gln Pro Pro Asp His Ile Pro Trp Ile Thr Ala
                485                 490                 495

Val Leu Pro Thr Val Ile Ile Cys Val Met Val Phe Cys Leu Ile Leu
            500                 505                 510

Trp Lys Trp Lys Lys Lys Arg Pro Arg Asn Ser Tyr Lys Cys Gly
        515                 520                 525

Thr Asn Thr Met Glu Arg Glu Glu Ser Glu Gln Thr Lys Lys Arg Glu
    530                 535                 540

Lys Ile His Ile Pro Glu Arg Ser Asp Glu Ala Gln Arg Val Phe Lys
545                 550                 555                 560

Ser Ser Lys Thr Ser Ser Cys Asp Lys Ser Asp Thr Cys Phe
                565                 570
```

<210> SEQ ID NO 28
<211> LENGTH: 444
<212> TYPE: PRT
<213> ORGANISM: Artificial Sequence
<220> FEATURE:
<223> OTHER INFORMATION: Synthesized

<400> SEQUENCE: 28

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
        115                 120                 125

Asn Gln Leu Tyr Asn Glu Leu Asn Leu Gly Arg Arg Glu Glu Tyr Asp
    130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205
```

Lys Asp Thr Tyr Asp Ala Leu His Met Gln Ala Leu Pro Pro Arg Gly
            210                 215                 220

Ser Gly Ala Thr Asn Phe Ser Leu Leu Lys Gln Ala Gly Asp Val Glu
225                 230                 235                 240

Glu Asn Pro Gly Pro Met Thr Leu His Pro Ser Pro Ile Thr Cys Glu
                245                 250                 255

Phe Leu Phe Ser Thr Ala Leu Ile Ser Pro Lys Met Cys Leu Ser His
                260                 265                 270

Leu Glu Asn Met Pro Leu Ser His Ser Arg Thr Gln Gly Ala Gln Arg
            275                 280                 285

Ser Ser Trp Lys Leu Trp Leu Phe Cys Ser Ile Val Met Leu Leu Phe
290                 295                 300

Leu Cys Ser Phe Ser Trp Leu Ile Phe Ile Phe Leu Gln Leu Glu Thr
305                 310                 315                 320

Ala Lys Glu Pro Cys Met Ala Lys Phe Gly Pro Leu Pro Ser Lys Trp
                325                 330                 335

Gln Met Ala Ser Ser Glu Pro Pro Cys Val Asn Lys Val Ser Asp Trp
            340                 345                 350

Lys Leu Glu Ile Leu Gln Asn Gly Leu Tyr Leu Ile Tyr Gly Gln Val
            355                 360                 365

Ala Pro Asn Ala Asn Tyr Asn Asp Val Ala Pro Phe Glu Val Arg Leu
            370                 375                 380

Tyr Lys Asn Lys Asp Met Ile Gln Thr Leu Thr Asn Lys Ser Lys Ile
385                 390                 395                 400

Gln Asn Val Gly Gly Thr Tyr Glu Leu His Val Gly Asp Thr Ile Asp
                405                 410                 415

Leu Ile Phe Asn Ser Glu His Gln Val Leu Lys Asn Asn Thr Tyr Trp
            420                 425                 430

Gly Ile Ile Leu Leu Ala Asn Pro Gln Phe Ile Ser
            435                 440

<210> SEQ ID NO 29
<211> LENGTH: 499
<212> TYPE: PRT
<213> ORGANISM: Artificial Sequence
<220> FEATURE:
<223> OTHER INFORMATION: Synthesized

<400> SEQUENCE: 29

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
                100                 105                 110

Val Lys Phe Ser Arg Ser Ala Asp Ala Pro Ala Tyr Gln Gln Gly Gln
            115                 120                 125

```
Asn Gln Leu Tyr Asn Glu Leu Asn Leu Gly Arg Arg Glu Glu Tyr Asp
            130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
            195                 200                 205

Lys Asp Thr Tyr Asp Ala Leu His Met Gln Ala Leu Pro Pro Arg Gly
210                 215                 220

Ser Gly Ala Thr Asn Phe Ser Leu Leu Lys Gln Ala Gly Asp Val Glu
225                 230                 235                 240

Glu Asn Pro Gly Pro Met Glu Tyr Ala Ser Asp Ala Ser Leu Asp Pro
                245                 250                 255

Glu Ala Pro Trp Pro Pro Ala Pro Arg Ala Arg Ala Cys Arg Val Leu
            260                 265                 270

Pro Trp Ala Leu Val Ala Gly Leu Leu Leu Leu Leu Leu Leu Ala Ala
            275                 280                 285

Ala Cys Ala Val Phe Leu Ala Cys Pro Trp Ala Val Ser Gly Ala Arg
290                 295                 300

Ala Ser Pro Gly Ser Ala Ala Ser Pro Arg Leu Arg Glu Gly Pro Glu
305                 310                 315                 320

Leu Ser Pro Asp Asp Pro Ala Gly Leu Leu Asp Leu Arg Gln Gly Met
                325                 330                 335

Phe Ala Gln Leu Val Ala Gln Asn Val Leu Leu Ile Asp Gly Pro Leu
            340                 345                 350

Ser Trp Tyr Ser Asp Pro Gly Leu Ala Gly Val Ser Leu Thr Gly Gly
            355                 360                 365

Leu Ser Tyr Lys Glu Asp Thr Lys Glu Leu Val Val Ala Lys Ala Gly
370                 375                 380

Val Tyr Tyr Val Phe Phe Gln Leu Glu Leu Arg Arg Val Val Ala Gly
385                 390                 395                 400

Glu Gly Ser Gly Ser Val Ser Leu Ala Leu His Leu Gln Pro Leu Arg
                405                 410                 415

Ser Ala Ala Gly Ala Ala Ala Leu Ala Leu Thr Val Asp Leu Pro Pro
            420                 425                 430

Ala Ser Ser Glu Ala Arg Asn Ser Ala Phe Gly Phe Gln Gly Arg Leu
            435                 440                 445

Leu His Leu Ser Ala Gly Gln Arg Leu Gly Val His Leu His Thr Glu
450                 455                 460

Ala Arg Ala Arg His Ala Trp Gln Leu Thr Gln Gly Ala Thr Val Leu
465                 470                 475                 480

Gly Leu Phe Arg Val Thr Pro Glu Ile Pro Ala Gly Leu Pro Ser Pro
                485                 490                 495

Arg Ser Glu

<210> SEQ ID NO 30
<211> LENGTH: 547
<212> TYPE: PRT
<213> ORGANISM: Artificial Sequence
<220> FEATURE:
<223> OTHER INFORMATION: Synthesized
```

<400> SEQUENCE: 30

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
    50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Gly Gly Cys Glu Leu Arg
                100                 105                 110

Val Lys Phe Ser Arg Ser Ala Asp Ala Pro Ala Tyr Gln Gln Gly Gln
            115                 120                 125

Asn Gln Leu Tyr Asn Glu Leu Asn Leu Gly Arg Arg Glu Glu Tyr Asp
130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
            195                 200                 205

Lys Asp Thr Tyr Asp Ala Leu His Met Gln Ala Leu Pro Pro Arg Gly
210                 215                 220

Ser Gly Ala Thr Asn Phe Ser Leu Leu Lys Gln Ala Gly Asp Val Glu
225                 230                 235                 240

Glu Asn Pro Gly Pro Met Arg Leu Gly Ser Pro Gly Leu Leu Phe Leu
                245                 250                 255

Leu Phe Ser Ser Leu Arg Ala Asp Thr Gln Glu Lys Glu Val Arg Ala
            260                 265                 270

Met Val Gly Ser Asp Val Glu Leu Ser Cys Ala Cys Pro Glu Gly Ser
            275                 280                 285

Arg Phe Asp Leu Asn Asp Val Tyr Val Tyr Trp Gln Thr Ser Glu Ser
    290                 295                 300

Lys Thr Val Val Thr Tyr His Ile Pro Gln Asn Ser Ser Leu Glu Asn
305                 310                 315                 320

Val Asp Ser Arg Tyr Arg Asn Arg Ala Leu Met Ser Pro Ala Gly Met
                325                 330                 335

Leu Arg Gly Asp Phe Ser Leu Arg Leu Phe Asn Val Thr Pro Gln Asp
            340                 345                 350

Glu Gln Lys Phe His Cys Leu Val Leu Ser Gln Ser Leu Gly Phe Gln
            355                 360                 365

Glu Val Leu Ser Val Glu Val Thr Leu His Val Ala Ala Asn Phe Ser
            370                 375                 380

Val Pro Val Val Ser Ala Pro His Ser Pro Ser Gln Asp Glu Leu Thr
385                 390                 395                 400

Phe Thr Cys Thr Ser Ile Asn Gly Tyr Pro Arg Pro Asn Val Tyr Trp
```

```
                        405                 410                 415
Ile Asn Lys Thr Asp Asn Ser Leu Leu Asp Gln Ala Leu Gln Asn Asp
                420                 425                 430

Thr Val Phe Leu Asn Met Arg Gly Leu Tyr Asp Val Ser Val Leu
            435                 440                 445

Arg Ile Ala Arg Thr Pro Ser Val Asn Ile Gly Cys Cys Ile Glu Asn
        450                 455                 460

Val Leu Gln Gln Asn Leu Thr Val Gly Ser Gln Thr Gly Asn Asp
465                 470                 475                 480

Ile Gly Glu Arg Asp Lys Ile Thr Glu Asn Pro Val Ser Thr Gly Glu
                485                 490                 495

Lys Asn Ala Ala Thr Trp Ser Ile Leu Ala Val Leu Cys Leu Leu Val
                500                 505                 510

Val Val Ala Val Ala Ile Gly Trp Val Cys Arg Asp Arg Cys Leu Gln
                515                 520                 525

His Ser Tyr Ala Gly Ala Trp Ala Val Ser Pro Glu Thr Glu Leu Thr
                530                 535                 540

Gly His Val
545

<210> SEQ ID NO 31
<211> LENGTH: 15
<212> TYPE: PRT
<213> ORGANISM: Artificial Sequence
<220> FEATURE:
<223> OTHER INFORMATION: Synthesized

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 281
<212> TYPE: PRT
<213> ORGANISM: Artificial Sequence
<220> FEATURE:
<223> OTHER INFORMATION: Synthesized

<400> SEQUENCE: 32

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
                20                  25                  30

Ala Ser Leu Glu Glu Ile Val Thr Ile Thr Cys Lys Ala Ser Gln Ala
            35                  40                  45

Ile Asp Ala Tyr Leu Ser Trp Tyr Gln Gln Lys Pro Gly Lys Ser Pro
        50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
                100                 105                 110

Ser Thr Pro Phe Thr Phe Gly Ser Gly Thr Lys Leu Glu Ile Lys Gly
            115                 120                 125

Gly Gly Gly Gly Ser Gly Gly Gly Ser Gly Gly Gly Gly Ser Met
        130                 135                 140
```

-continued

```
Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
                180                 185                 190

Ser Asn Ser Val Ser Trp Ile Arg Gln Pro Pro Gly Lys Gly Leu Glu
            195                 200                 205

Trp Met Gly Val Ile Trp Ser Asn Gly Asp Ala Asp Tyr Asn Ser Ala
        210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255

Cys Ala Ser Pro Tyr Tyr Gly Tyr Tyr Phe Pro Phe Asp Tyr Trp Gly
                260                 265                 270

Gln Gly Val Met Val Thr Val Ser Ser
                275                 280
```